United States Patent [19]

Catsimpoolas et al.

[11] Patent Number: 4,921,838
[45] Date of Patent: May 1, 1990

[54] ANGIOGENIC AND BLOOD PERFUSION INDUCING PROPERTIES OF AMPHIPHILIC COMPOUNDS

[75] Inventors: Nicholas Catsimpoolas; Ann L. Griffith, both of Newton Centre, Mass.; Robert S. Sinn, New York, N.Y.

[73] Assignees: Trustees of Boston University, Boston, Mass.; Angio-Medical Corp., New York, N.Y.

[21] Appl. No.: 62,962

[22] Filed: Jun. 16, 1987

[51] Int. Cl.$^5$ .............. A61K 31/70; A01N 43/04; A01N 57/00; C07J 00/00
[52] U.S. Cl. .................. 514/25; 514/75; 514/53; 536/6.0; 536/4.1; 558/38; 558/48; 568/622; 568/608; 549/478; 260/403; 564/291
[58] Field of Search .............. 514/25, 75, 53; 536/6.0, 4.1; 558/38, 48; 568/622, 608; 549/478; 260/397.2, 403; 564/291

[56] References Cited

U.S. PATENT DOCUMENTS

| | | | |
|---|---|---|---|
| 3,975,536 | 8/1976 | Stevenson et al. | 514/456 |
| 4,053,628 | 10/1977 | Stevenson et al. | 514/456 |
| 4,242,502 | 12/1980 | Malinow et al. | 536/5 |
| 4,511,564 | 4/1985 | Ishizuka et al. | 514/167 |
| 4,602,003 | 7/1986 | Malinow | 514/169 |
| 4,636,497 | 1/1987 | Niemers et al. | 514/224.5 |
| 4,681,876 | 7/1987 | Marples et al. | 514/182 |
| 4,710,490 | 12/1987 | Catsimpoolas et al. | 514/25 |
| 4,767,746 | 8/1988 | Catsimpoolas et al. | 514/25 |

*Primary Examiner*—Ronald W. Griffin
*Assistant Examiner*—Pamela S. Webber
*Attorney, Agent, or Firm*—Felfe & Lynch

[57] ABSTRACT

A method for enhancing angiogenesis and/or blood vascular perfusion in mammals by administering a pharmacologically effective amount of specific angiogenically active non-ionic, anionic, cationic and zwitterionic amphiphilic compounds. An angiogenically effective amount of the angiogenically active compound digitonin is in the range of at least 1.25 microgram to at least 200 microgram of digitonin. The range including enhancement of vascular perfusion is up to 50 mg of digitonin.

8 Claims, 13 Drawing Sheets

ANGIOGENIC AND BLOOD PERFUSION INDUCING PROPERTIES OF AMPHIPHILIC COMPOUNDS

FIELD OF THE INVENTION

This invention relates to amphiphilic compounds having angiogenic and blood perfusion inducing properties. In particular, amphiphilic compounds having non-ionic, anionic, cationic and zwitterionic characteristics have been tested for positive angiogenic and blood perfusion inducing activity.

BACKGROUND OF THE INVENTION

Angiogenesis is the process by which new blood vessels are formed, with accompanying increased blood circulation. The field of angiogenesis has been a favorite for research and investigation for over one hundred years. See, e.g. Virchau, R., *Die Krankhaftern Geshwultste, Hirshwald*, Berlin (1863); Thiersch, C., *Die Haut Mit Atlas*, Leipzig (1865); (significance of the interaction between host vasculature and survival and growth of solid malignant tumors observed). Interest has been fueled by the observation that angiogenic factors are found, in trace amounts, in normal tissue. See, e.g., D'Amore et al., *PNAS* 78:3068-3072 (1981); Kissun, et al., *Br. J. Ophthalmol.* 66:165-169 (1982); (retinal tissue); DeCarvallho, et al., *Angiology* 34:231-243 (1983); (activated lymphocytes and macrophages); Frederick, et al., *Science* 224:289-390 (1984); (human follicular fluid); Burgos, *Eur. J. Clin. Invest.* 13:289-296 (1983); (amniochorion and placenta); Castellot, et al *PNAS* 79:5597-5601 (1982); (culture medium of 3T3 cells). The trace amounts of angiogenic factors observed in these tissues do not, however, show any angiogenic activity other than in normal growth and development of tissues and organs. Similarly, angiogenic factors have been observed in tissues of pathological origin. See, e.g., Weiss, et al., *Br. J. Cancer* 40:493-496 (1979); Fencelau, et al., *J. Biol. Chem.* 256:9605-9611 (1981), McAslau, et al., *Exp. Cell Res.* 119:181-190 (1979); (tumor cells); Kumar, et al., *Lancet* 2:364-367 (1983); Brown, et al., *Lancet* 1:682-685 (1980) (synovial fluid of arthritis patients); Hill, et al., *Experientia* 39:583-585 (1983) (vitreous material of diabetics); Banda, et al., *PNAS* 79:7773-7777 (1982) (wound fluid).

Goldsmith et al, (1984) *JAMA* 252: 2034-2036 is the first report of an angiogenic factor which shows activity beyond normal growth and development, and is available in large quantities. The factor was found in chloroform/methanol fractionates of feline omenta (CMFr). See the co-pending application Ser. No. 642,624, filed Aug. 20, 1984, entitled "Angiogenesis Factor and Method for Producing Angiogenesis," of Catsimpoolas and Goldsmith. This application is incorporated by reference herein.

It has further been found that the crude lipid extract of Goldsmith et al. (1984), Supra may be purified into various fractions which possess angiogenic properties far above those observed in the CMFr.

Additionally, it has been found that commercially available gangliosides such as gangliosides derived from brain tissue and other lipid containing compounds also possess angiogenic properties. Further, new compositions of known lipid containing compounds may be formed which also possess angiogenic properties.

The discovery of lipid containing compounds which possess angiogenic properties is relatively new to the art. Previously attention has been focused on proteinaceous angiogenic factors. See, e.g., Kumar et al., Lancet II:364-367 (1983) (proteinaceous factors from 300 to $10^5$ daltons); Kissun, et al., supra (proteinaceous factors up to 70 kd); Banda, et al., supra (proteins of about 2-14 kd); Burgos, et al., supra, (protein complexes of from 100-200 kd). It has now been unexpectedly shown that compositions containing lipid containing molecules, such as gangliosides, glycolipids, ceramides, cerebrosides, phospholipids, sphingosides, and so forth, exhibit enhanced angiogenic activity as disclosed in co-pending U.S. patent application Ser. No. 782,724, filed Oct. 1, 1985 and incorporated by reference herein.

Angiogenic lipid containing compounds are known to increase vascular perfusion in wound areas of test animals as described in co-pending U.S. patent application Ser. No. 805,206 filed on Dec. 4, 1985 and incorporated herein by reference. Also see Goldsmith, et al., *Surgery* 162:579-583 (Jun. 1986) and *JAMA* 252: at 2035 (1984).

The lipid containing compounds have also been found to exhibit unexpected results when used to treat angina and myocardial infarctions as disclosed in U.S. patent application, Ser. No. 811,375, filed on Dec. 20, 1985 and incorporated by reference herein. Tests have shown, for example, that vascularization, neovascularization and vascular collateralization are accelerated. This is a surprising result since lipid materials are regarded more as atherosclerotic agents than vascularizing agents in heart tissue.

Lipids are displaced from homogenized cell membranes, or other complexes involving proteins by detergent molecules which render the proteins "soluble" in aqueous media as discussed in co-pending U.S. patent application, Ser. No. 805,206, filed on Dec. 4, 1985 and incorporated by reference herein. Also see Colombo, M. I. et al. Biol. Cell 54:73 (1985) or Chuang, D. M., et al. J. Cyclic Nucleotide Protein Phosphor Res. (U.S.) 10:281 (1985) and Wall, D. A. et J. Cell. Biol. 101:2104 (1985). One theory proposed, but in no way intended to limit the inventors to just this theory is that amphiphilic compounds or detergents, used to "solubilize" the lipid components from the cell surface may indirectly induce angiogenesis since angiogenic lipids, such as phospholipids, glycolipids, and gangliosides, are found on biological membranes. See co-pending U.S. application, Ser. No. 782,724, supra.

Since most amphiphilic compounds aggregate in aqueous media to form micelles above certain concentrations called the "critical micellar concentration" (CMC), they have been found to be effective in dissolving lipids from biological membranes mainly by forming mixed micelles with lipids. See, e.g., Lichtenberg, et al., *Biochim. Biophys. Acta*, 737: 285-304 (1983); (structural and kinetic aspects of solubilization of phospholipids by detergents); Helenius, et al., *Biochim. Biophys. Acta*, 415:29-79 (1975); (solubilization of membranes by detergents); and Hjelmeland, L. M., *Methods in Enzymology*, 124:135-164 (1986); (design and synthesis of detergents for membrane biochemistry).

The art supports some use of amphililic compounds in biological situations. We refer to the work of Pitha and Szente in the Journal of Pharmaceutical Sciences 73:240 (1984) wherein derivatives of digitonin are formed which lower amphiphilic compound toxicity. In that work $CH_2OH$ groups of digitonin were converted to $CH_2OH_2CHOHCH_3$ or to $CH_2OCH_2CHOHC$-

H$_2$O(CH$_2$)$_4$OCH$_2$CHOHCH$_2$OH groups. We note the toxicity varies greatly from species to species and in mode of use, Pitha and Szente ibid P. 242. Pat. No. 4,546,097 issued Oct. 8, 1985 to Josef Pitha discusses mycoplasma suppression in culture and increased solubilization of lipophilic drugs. However there is no angiogenic effect taught therein.

The angiogenic results of the invention are therefore surprising since as reported in the above paper by Pitha and Szente, digitonin has been known for some inflammatory and hemolytic effects.

The work of Segel et al. (1977) Biochem. Pharm. 26:643 discusses protection against the hemolytic effect of digitonin using a specific saponin, glycyrrhizin (P. 644). Digitonin has been used to prevent hypercholesterolemia in monkeys Malinow, M. R., et al. (1978) Amer. J. Clin. Nutrition 31:814. Cholesterol adsorption regulation in humans with digitonin is the subject of a Malinow et al. U.S. Pat. No. 4,242,502. Generally digitonin forms insoluble complexes with cholesterol.

Digitonin was tolerated by both rats and monkeys in that work (see P. 817). We also note that a mixture of digitonin glucosides comprise the commercial material. Therefore the angiogenic effect may be expected for all congeners therein as detailed by Y. M. Yang et al. (1986) Biomedical and Environmental Mass Spectroscopy 13:439.

It is thus an object of this invention to describe specific amphiphilic compounds and their use to enhance angiogenesis and blood perfusion properties in mammals.

It has now been unexpectedly shown that particular amphiphilic compounds have angiogenic properties as discussed infra. The solubilization of lipid components by amphiphilic compounds from the surface of normal cells may indirectly induce angiogenesis.

SUMMARY OF THE INVENTION

Amphiphilic compounds have been shown to possess angiogenic and vascular perfusion enhancing properties. In particular, amphiphilic compounds having charged hydrophilic groups such as anionic, cationic and zwitterionic; uncharged but polar hydrophilic groups such as polyoxyethylene and polyhydroxy residues, and hydrophobic groups having aliphatic chains, polycyclic groups or aromatic moieties have been shown to possess such angiogenic activity.

Especially preferred amphiphilic compounds are: digitonin, N-octylglucoside, polyoxyethylene alcohol, polyoxyethylene p't'octyl phenol, n-dodecyl glucoside, dodecyl-beta-D-maltoside, deoxycholic acid, sodium dodecylsulfate; tetradecyltrimethylammonium bromide; sulfobetaine; 3-[(3-cholamido propyl)dimethylammonio]-1-propane sulphonate and lysophosphatidylcholine.

BRIEF DESCRIPTION OF THE DRAWINGS

FIGS. 3–13 graphically illustrate angiogenic activity by plotting DU values of CAM assays of specific amphiphilic compounds and corresponding to Tables V–XIII respectively.

DESCRIPTION OF THE DRAWINGS

Figure 1:
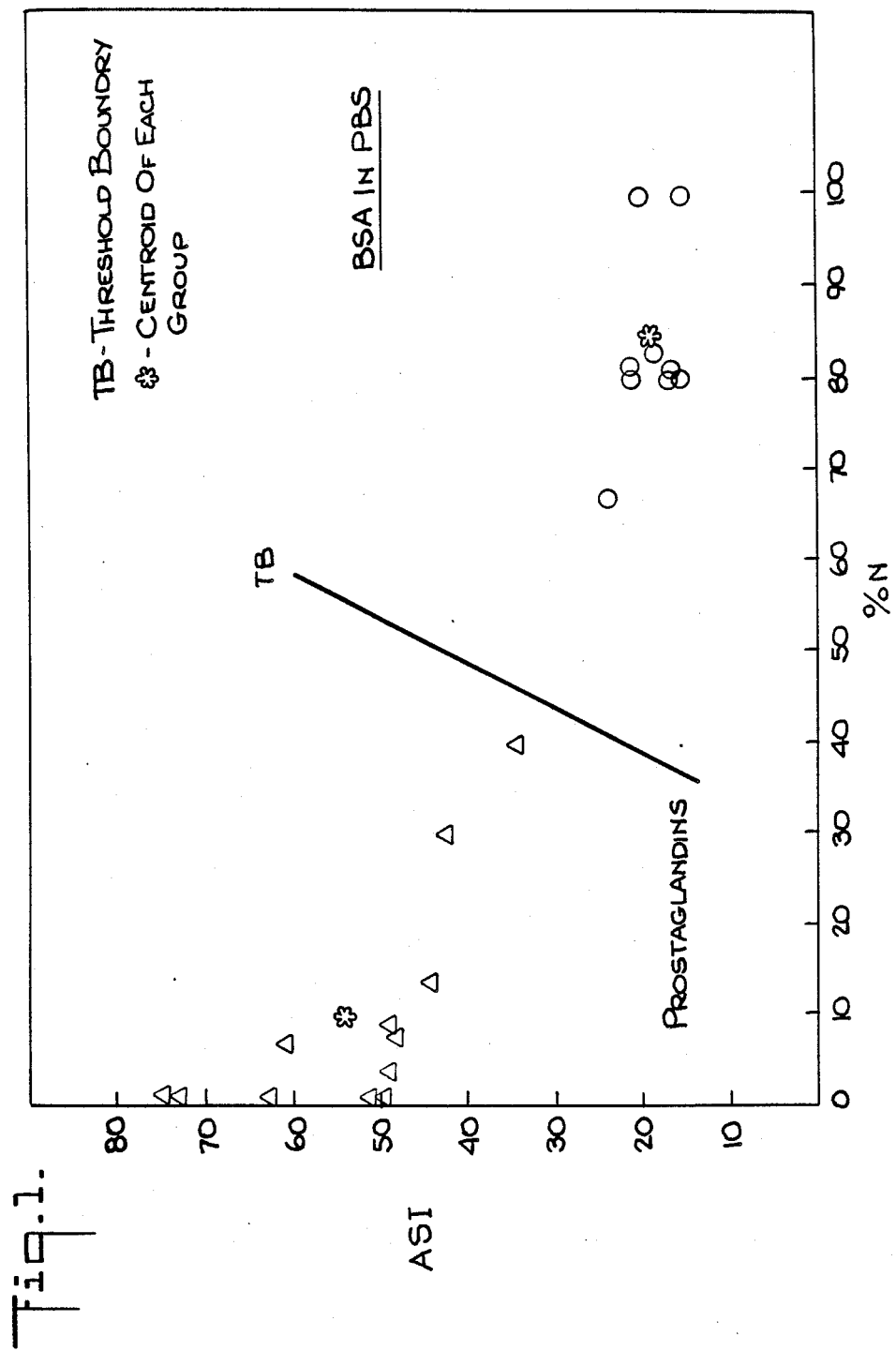
FIG. 1 graphically illustrates a bivariate distribution of CAM assay scores obtaining from angiogenically positive (prostaglandins) and negative (BSA in PBS) controls (Table IV).

FIG. 1. Bivariate distribution of CAM assay scores obtained from angiogenically positive (prostaglandins) and negative (BSA in PBS) controls. The separating line indicates the threshold boundary (TB) between the two groups. The asterisks indicate the position of the centroids for each group.

Figure 2:
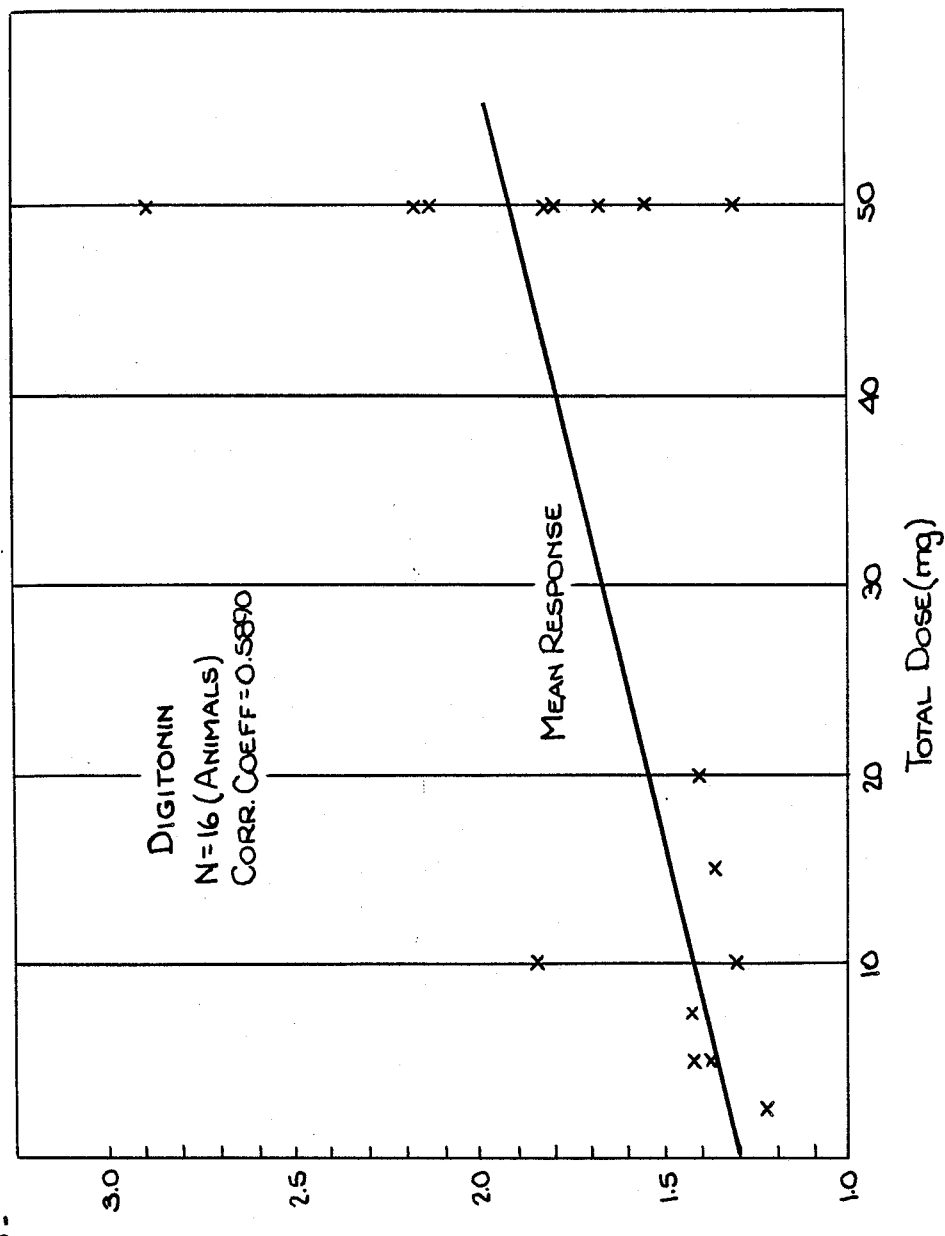
FIG. 2 graphically illustrates a dose-response of a specific amphiphilic compound digitonin showing an increase in vascular perfusion in surgically excised cats (Table III). Table III includes other compounds besides digitonin.

FIG. 2. Blood perfusion studies. Plot of radiodensity values versus total dose of digitonin injected i.m.

Figure 3:
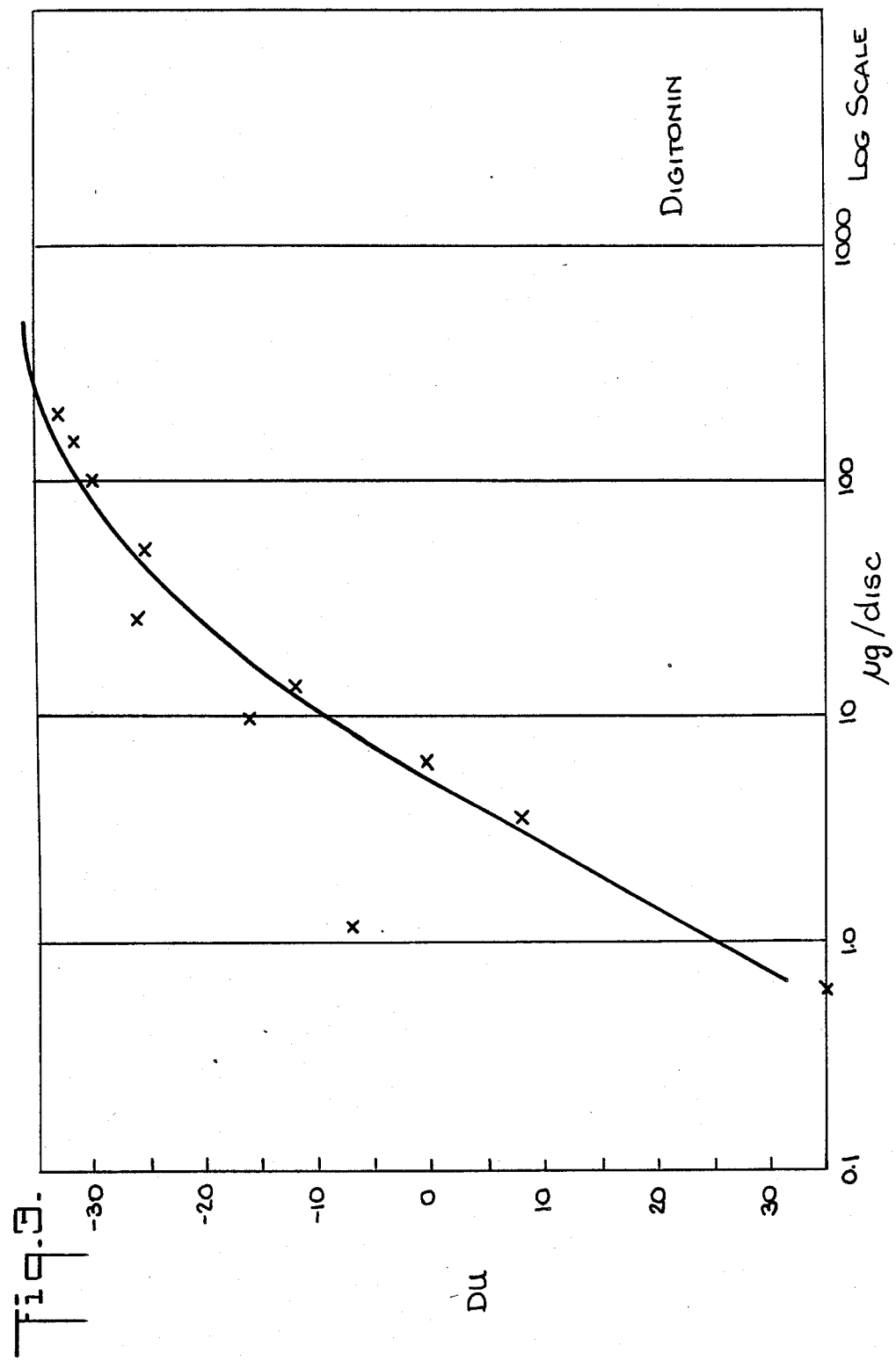

FIG. 3. Plot DU value obtained by applying the indicated amount of digitonin (ug/disc) on the CAM. (ug=microgram)

Figure 4:
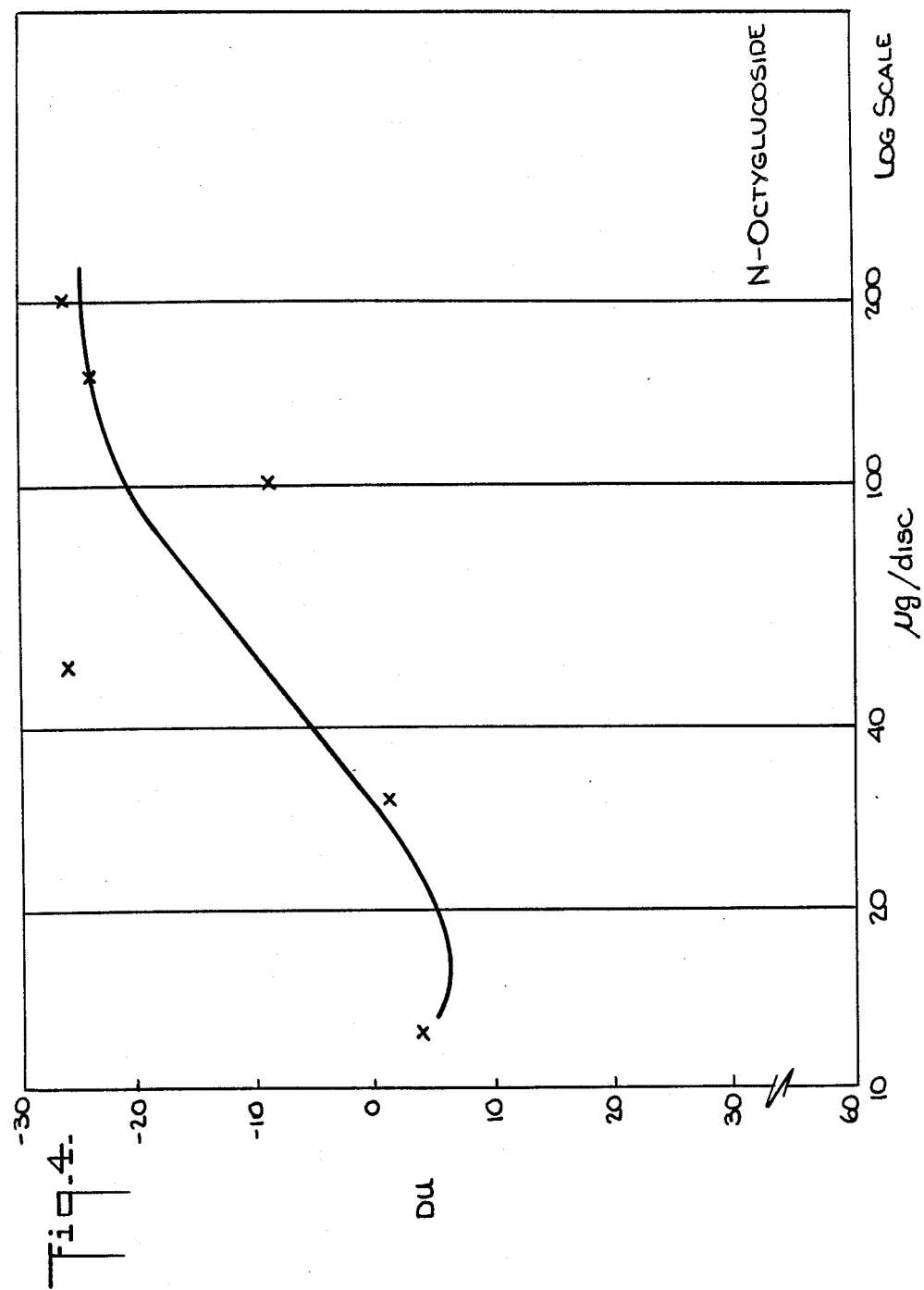

FIG. 4. Plot of DU value obtained by applying the indicated amount of N-octylglucoside (ug/disc) on the CAM.

Figure 5:
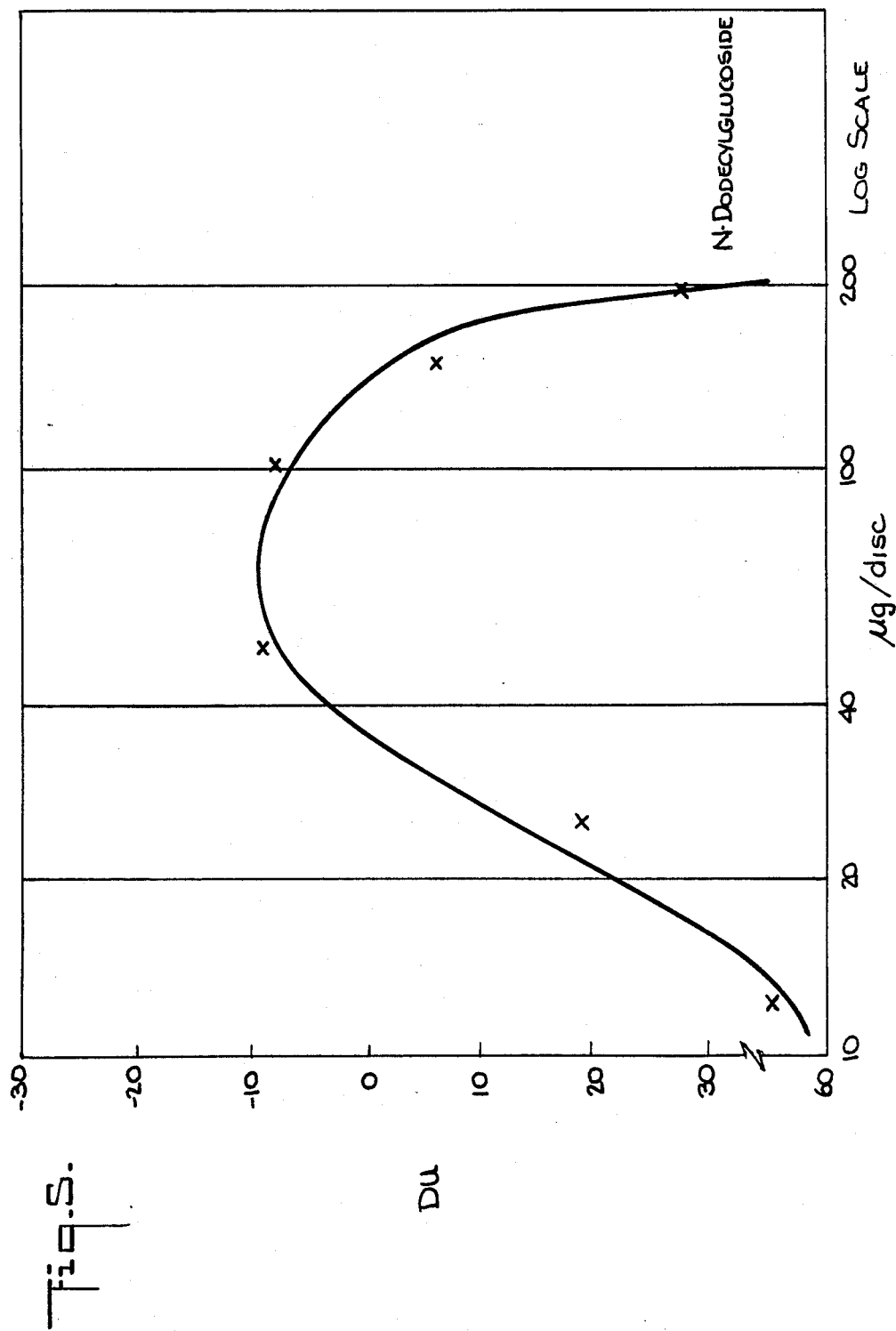

FIG. 5. Plot of DU value obtained by applying the indicated amount of N-dodeylglucoside (ug/disc) on the CAM.

Figure 6:
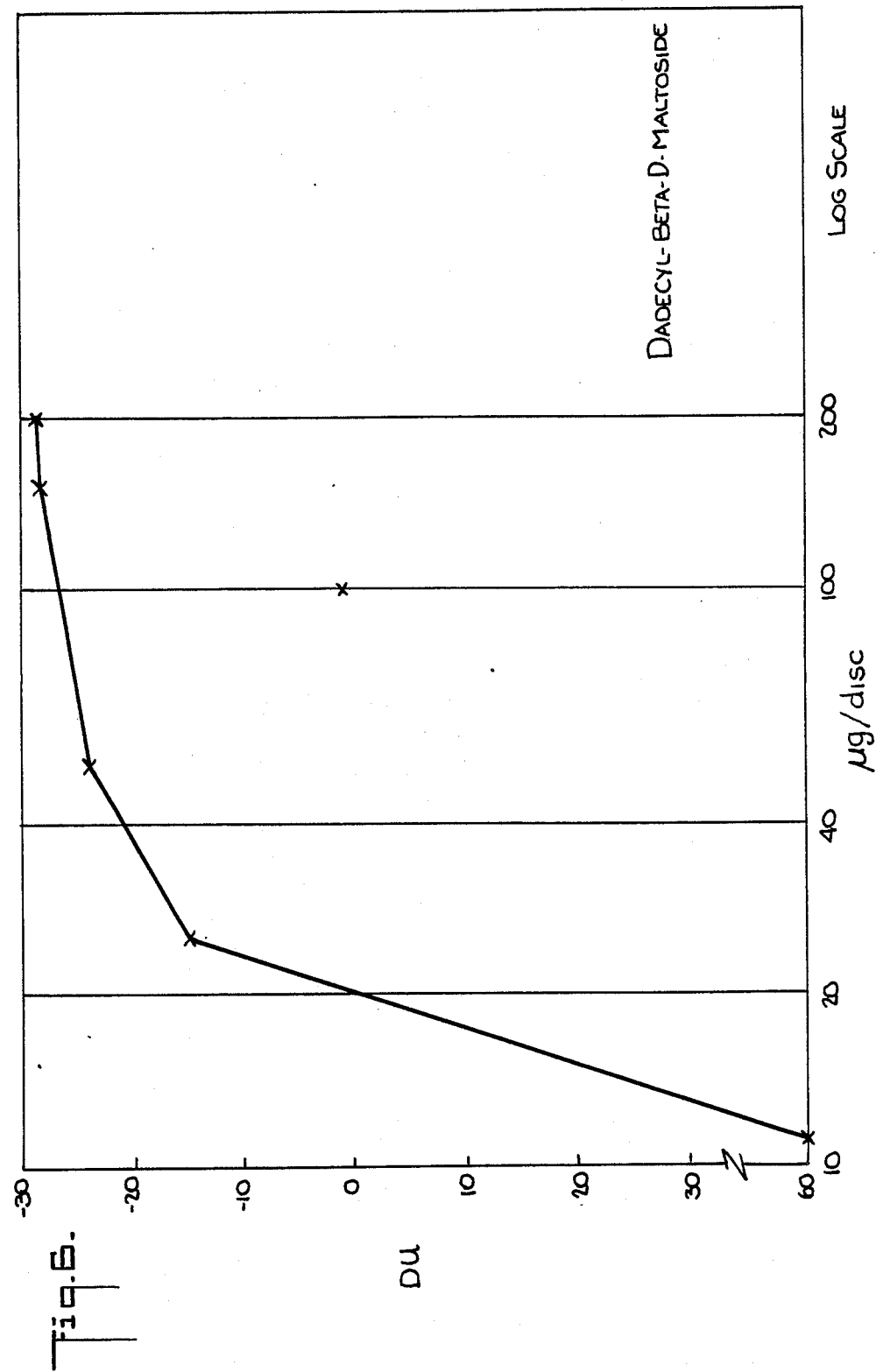

FIG. 6. Plot of DU value obtained by applying the indicated amount of Dodecyl-beta-D-maltoside (ug/disc) on the CAM.

Figure 7:
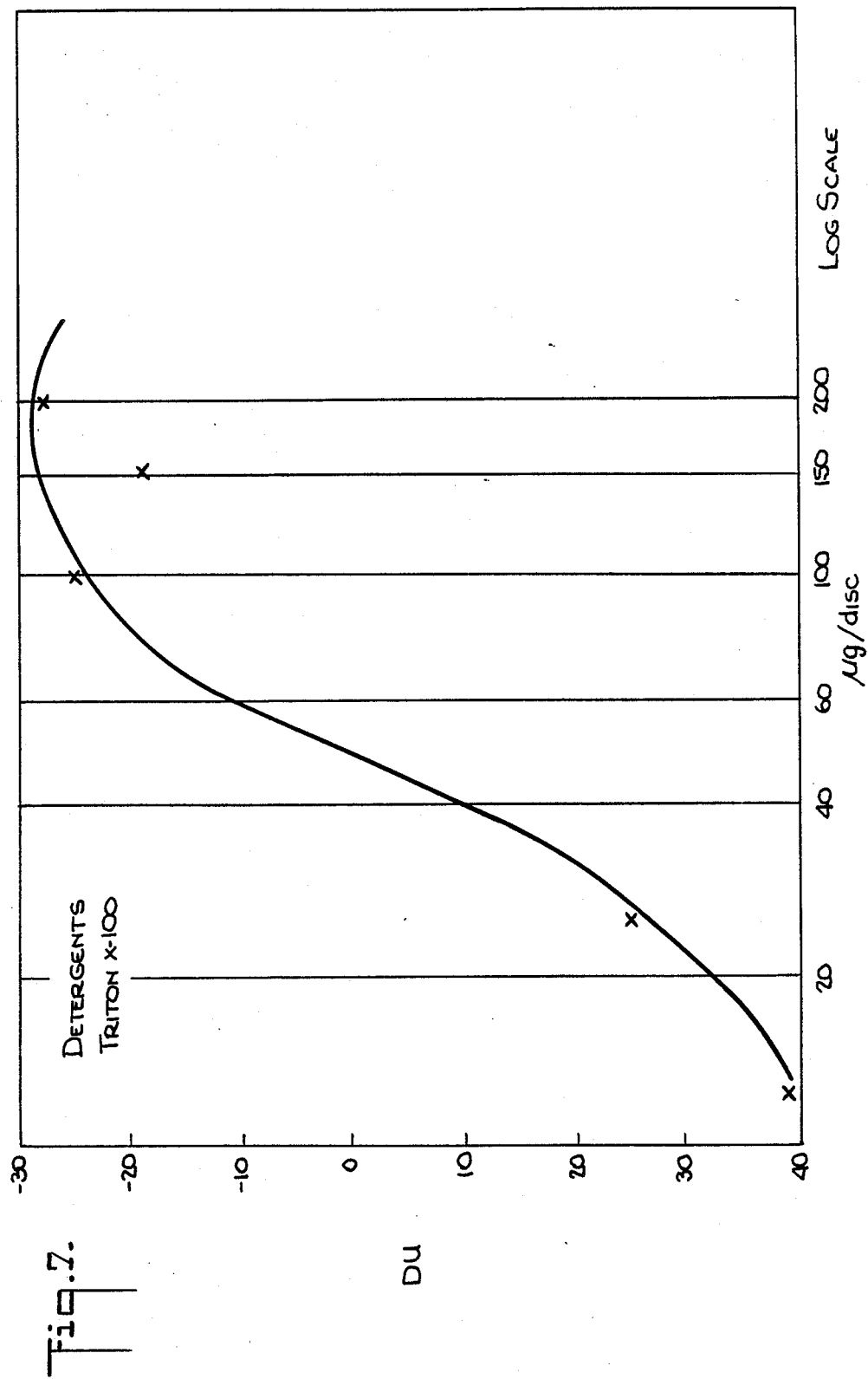

FIG. 7. Plot of DU value obtained by applying the indicated amount of Triton X-100 (polyoxyethylene p't'octyl phenol) (ug/disc) on the CAM.

FIG. 8. Plot of DU value obtained by applying the indicate amount of Nonidet P40 (polyoxyethylene p't'octyl phenol) (ug/disc) on the CAM.

Figure 9:
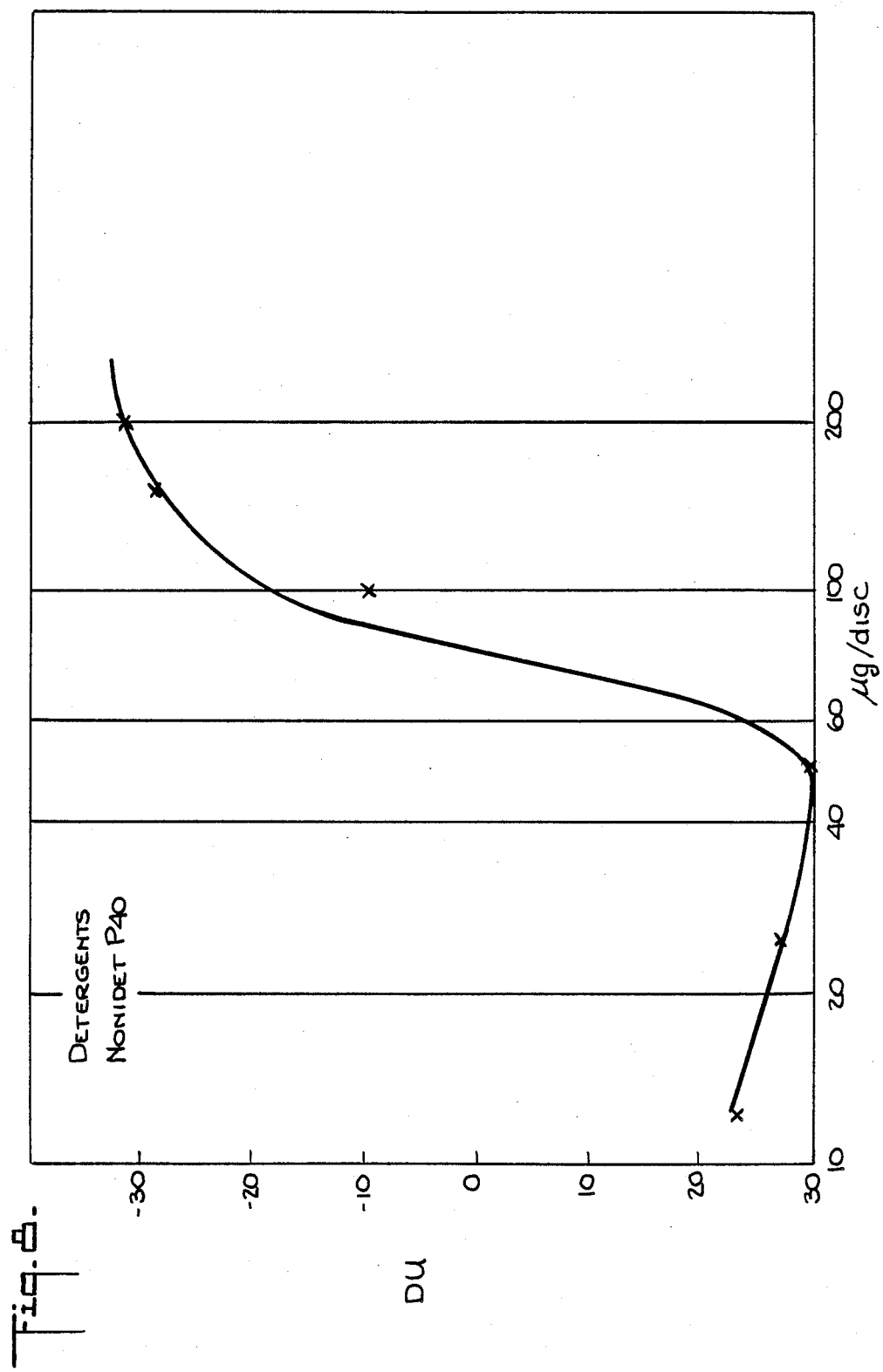
Figure 9:
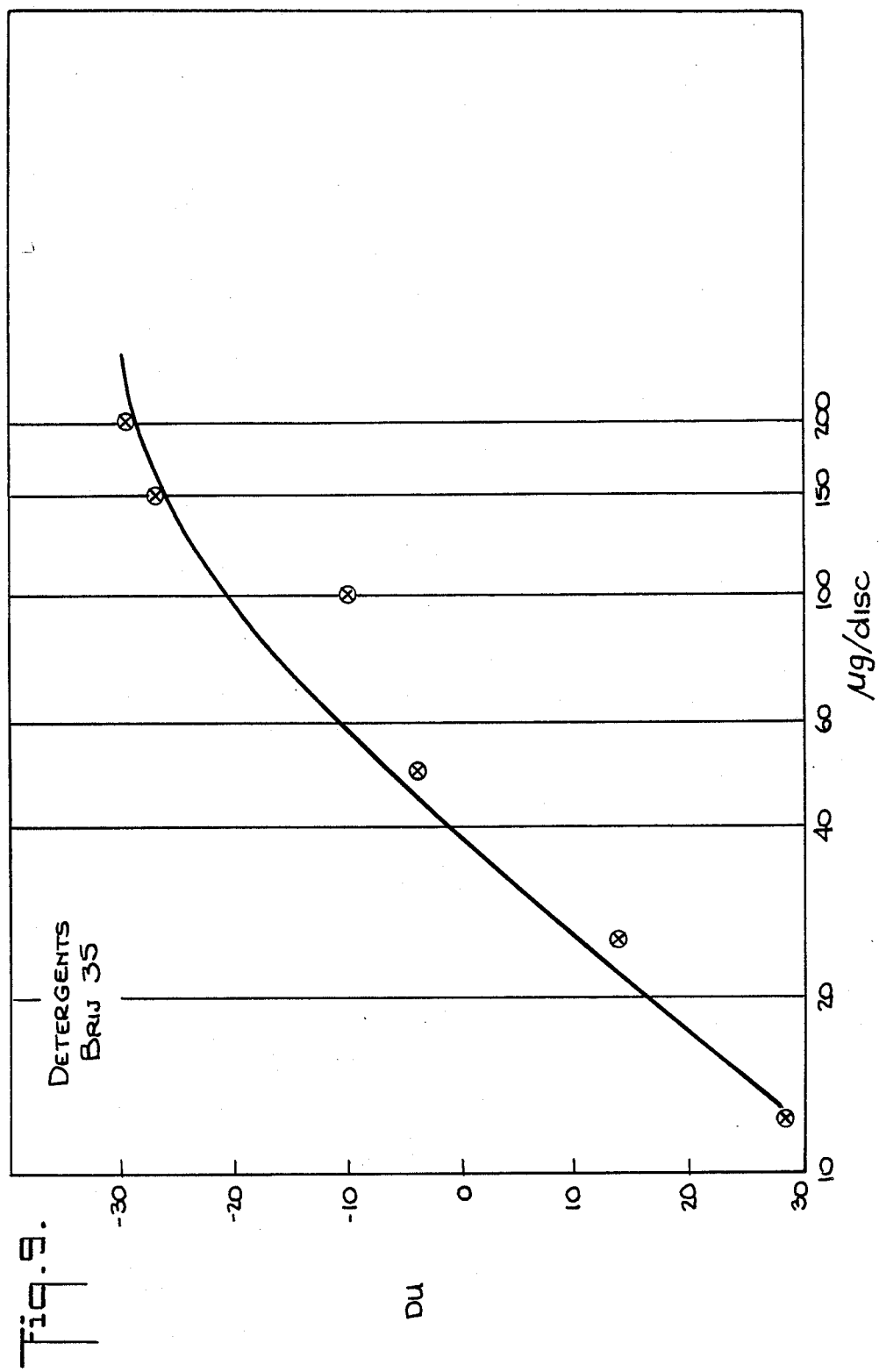

FIG. 9. Plot of DU value obtained by applying the indicated amount of BRIJ 35 (polyoxyethylene alcohol) (ug/disc) on the CAM.

Figure 10:
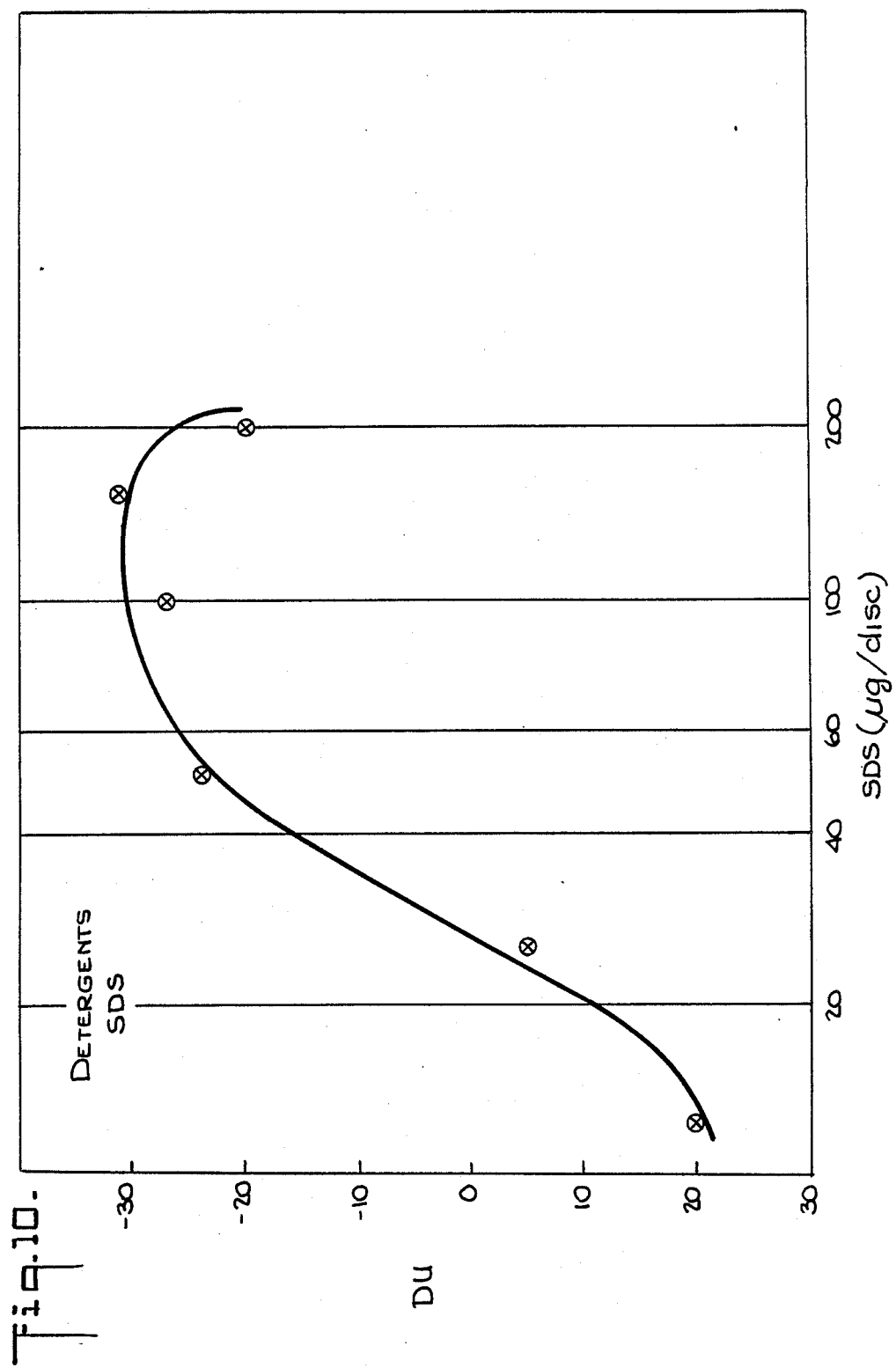

FIG. 10. Plot of DU value obtained by applying the indicated amount of SDS (ug/disc) on the CAM.

Figure 11:
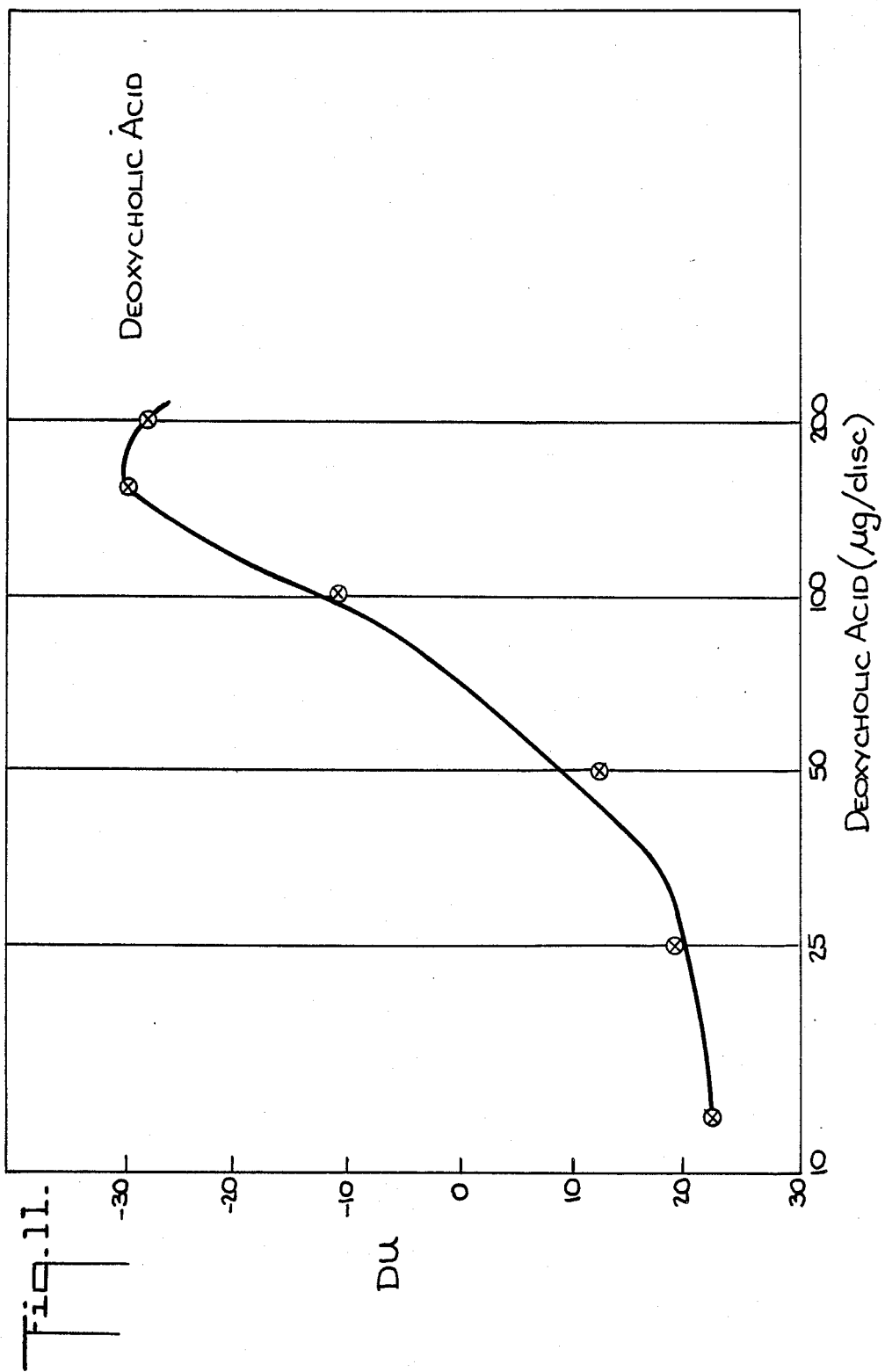

FIG. 11. Plot of DU value obtained by applying the indicated amount of Deoxycholic Acid (ug/disc) on the CAM.

Figure 12:
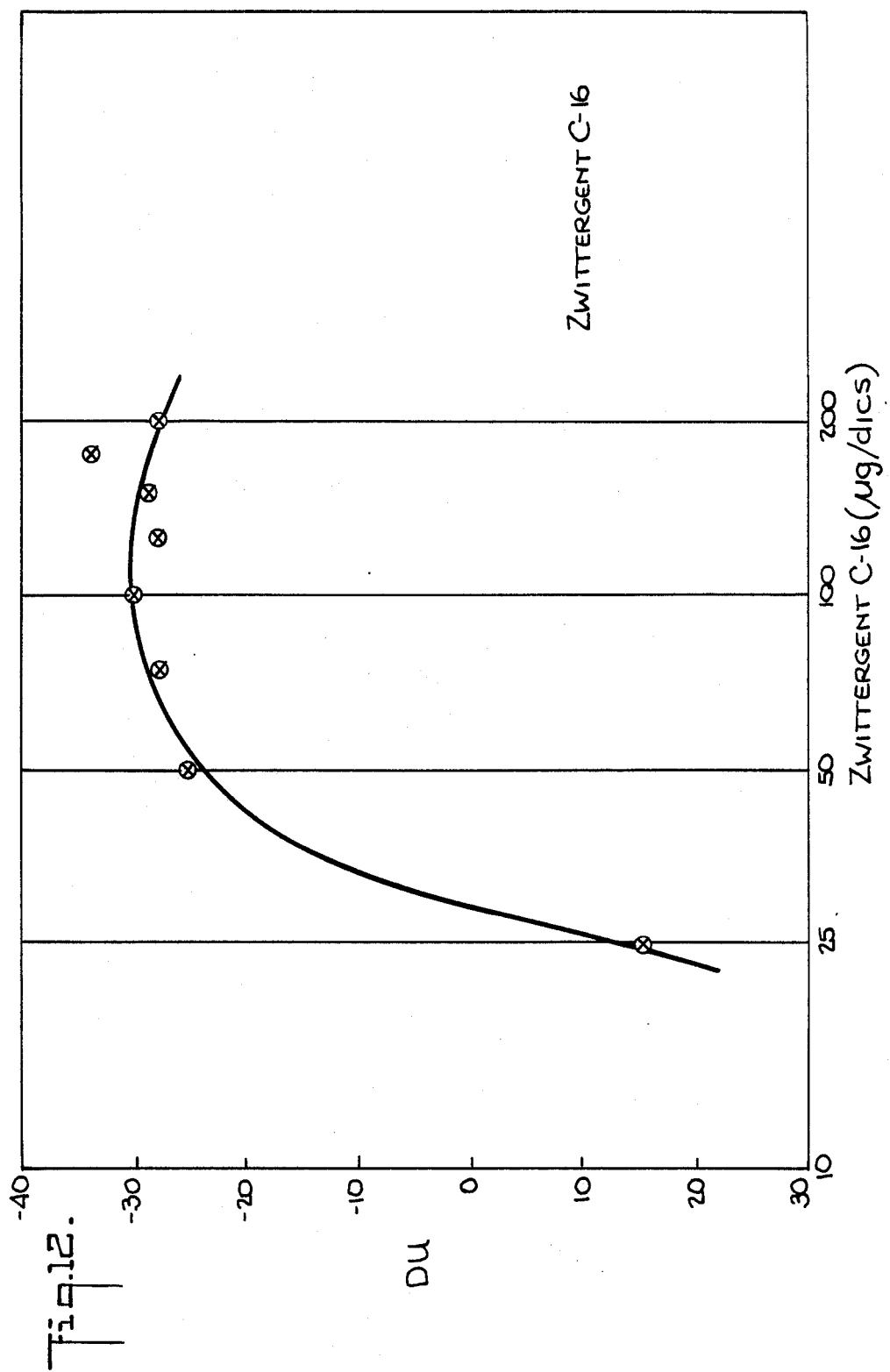

FIG. 12. Plot of DU value obtained by applying the indicated amount of Zwittergent (sulfobetaine) C-16 (ug/disc) on the CAM.

Figure 13:
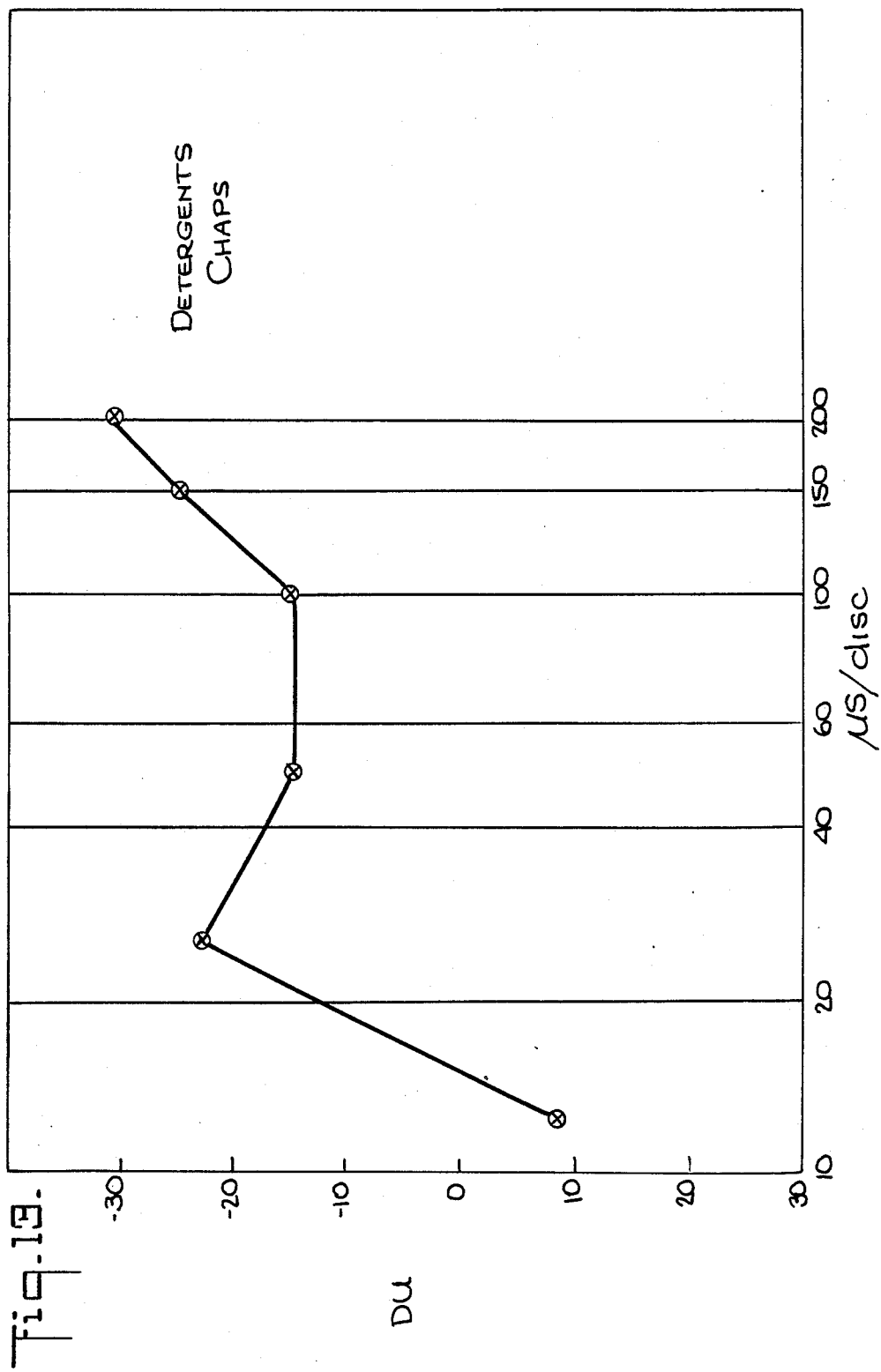

FIG. 13. Plot of DU value obtained by applying the indicated amount of CHAPS (3-[(3-cholamidopropyl)-dimethylammonio]-1-propanesulphonate) (ug/disc) on the CAM.

Description

Amphiphilic Compounds Tested By the Inventive Method.

In the present invention, the amphiphilic compounds which were tested for angiogenic activity are listed by their scientific names in Table I. The compounds were chosen from groups having both hydrophilic and hydrohpobic properties. Also included in Table I are the structural formula of the tested amphiphilic compounds.

The tested amphiphilic compounds were: digitonin, N-octylglucoside, polyoxyethylene alcohol, polyoxyethylene glycol sorbitol, polyoxyethylene p't'octyl phenol, n-dodecyl glucoside, dodecyl-beta-D-maltoside, deoxycholic acid, sodium dodecylsulfate; tetradecyltrimethylammonium bromide; sulfobetaines; 3-[(3-cholamido propyl)dimethylammonio]-1-propane sulphonates, lysophosphatidylcholine, cholic acid and taurocholic acid.

Also the compounds digitonin, sulfobetaine, polyoxyethylene glycol sorbitol, N-octylglucoside, and dodecyl-beta-D-maltoside were tested for their ability to enhance vascular blood perfusion in operated animals.

It is noted that when the compounds listed supra are marketed, the products are typically a mixture of compounds and not necessarily a pure form of the compound desired. For example, digitonin is marketed as a saponin mixture typically having four or more different structures of steroidal genins as illustrated in Table II.

Other amphiphilic compounds tested for angiogenesis are not as well studied as digitonin as to the variety of structures typically found in the commercially available products. In particular sulfobetaine is marketed under the generic names of Zwittergent C8, C10, C12, C14 and C16 by Behring Diagnostics, and polyoxyethylene glycol sorbitol may be marketed as Tween 20, 40, 60 or 80. Polyoxythylene p't'octyl phenol is marketed as Triton-X or Nonide P-40. Polyoxyethylene alcohol is marketed as Brij 35 and Lubrol P-X. 3-[(3-cholamidopropyl)dimethylammonio]-1-propanesulphonate is marketed as CHAPS. Therefore, reference to one structure of a compound in the application is not deemed limiting to only the structure discussed but extends to all possible structures of the compound found in a typical marketed mixture.

Commercial Sources of Detergents Tested

Sigma Chemical Co. (St. Louis, Mo.)
  Digitonin, Lubrol PX, deoxycholic acid, cholic acid, taurocholic acid, tetradecyltrimethylammonium bromide, lysophosphatidylcholine
Calbiochem (San Diego, Calif.)
  Triton X-100
Boehringer Mannheim Biochemicals (Indianapolis, Ind.)
  N-octylglucoside
  N-dodecyl glucoside
  dodecyl beta-D-Maltoside
Accurate Chemical and Scientific Corp (Westbury, N.Y.)
  Nonidet P40
Pierce Chemical Co. (Rockford, Ill.)
  Brij 35
Fisher Scientific (Fairlawn, N.J.)
  Tween 20, 40, 60, 80
Bio-Rad (Richmond, Calif.)
  Sodium dodecyl sulfate
Behring Diagnostics (La Jolla, Calif.)
  Zwittergent C8, C10, C12, C14, C16 CHAPS Chick Embryo Chorioallantoic Membrane (CAM) Assay.

For angiogenesis testing, aliquoted amounts of the amphiphilic compounds were dissolved in a solution of phosphate buffered saline (PBS) containing 1% bovine serum albumin (BSA). Two parts of these solutions were mixed with one part warm agarose solution (4%) in PBS and were allowed to solidify (gel) into pellets. The pellets having an approximate cross-sectional area of 3 millimeters square were then placed on the CAM for testing. The CAM assay system is found to be useful as it can be applied to the analysis of animal samples, mammalian samples and organic compounds and predict angiogenic activity for those systems.

CAM Scoring System

CAM Assays.

Angiogenic properties of the compounds were determined by subjecting these samples to a variant of the Chick Embryo Chorioallantoic Membrane Assays ("CAM assays") described in Folkman, J., Cancer Res. 34:2109 (1974 and Klagsburn, et al., Cancer Res. 36:110 (1976).

The CAM assay applied in the subject method uses fertile chicken eggs, and involves the following steps:

Preparing the Eggs: By using a power drill, a 2 cm square of shell is removed from the fertilized egg on day 4 of incubation. The opening is now referred to as a "window". Cellophane tape tightly seals off the window to the outside environment. The eggs are then put in the 37° C. incubator for another 4 days.

Making the Discs: On the 8th day after incubation, 0.4 g of agarose and 10 ml of PBS are mixed and heated to 100° C. with a 2% BSA solution (in PBS). The mixture (2% agarose plus 1% BSA in PBS) is kept warm in a water bath. Using a pipet 20 to 40 microliters (=micro) of the testing solution (i.e., extract, fractionate, or composition) is mixed with a drop of the agarose mixture by constant stirring. After the large disc is hardened by gelation, it is subdivided into 4 smaller discs.

Placing the Discs on the Membrane: On the 8th day after incubation, the discs are placed inside the eggs on the CAM; choosing areas on the CAM with various degrees of blood vessel development. The selected area is approximately 1 cm away from the chick embryo but not so far away that the disc will lie beyond the CAM or stick to the inside shell wall. The eggs are then incubated for another 4 days. All instruments used are previously soaked in 98% ethanol.

Rating the Effects: Upon the 12th day of incubation, the discs are located inside the eggs and the windows are made larger by breaking off bits of the shell with a pair of forceps.

The eggs are then examined under the light microscope. The vascularization in the rest of the egg is compared to that surrounding the disc. Degrees of neovascularization in the direction of the disc is determined and compared with the effects of the discs in other eggs. The effect of each disc is rated on a scale of 1 to 5, as follows:

0 = no response.

1 = one or two small areas of increased branching around the disc; essentially negative.

2 = three or more small areas of increased branching around the disc; a weak response.

3 = formation of "wheel spoke effect," which is self explanatory; increased branching around the disc; a moderate response.

4 = "wheel spoke effect" with increased branching around the disc, to a degree greater than in "3"; a strong response.

5 = "wheel spoke effect" with extensive branching around the disc; a very strong response.

Pluses and minuses are also used, with each numerical value, so a CAM assay could have a value ranging from 0 (no response whatsoever) to 5 (exceptionally strong response, with extensive branching).

Based upon the foregoing scoring system, an Angiogenic Scoring Index (ASI) for each test sample was derived from:

$$ASI = \frac{\text{Sum of scores on individual } CAM's}{\text{Sum of maximum possible scores}} \times 100$$

For example, in a sample containing 12 CAM assays, if seven were scored "2", one was scored "3", and four were negative ("0") the ASI index was:

$$ASI = \frac{7(2) + 1(3) + 4(0)}{12 \times 5} \times 100 = 28.3$$

A percent negative (% N) index for each sample was estimated from:

$$\%N = \frac{\text{Number of negative } CAM \text{ tests}}{\text{Number of all } CAM \text{ tests}} \times 100$$

and in the example above, $$\%N = \frac{4 \times 100}{12} = 33\%$$

The ASI score provides a measure of the intensity (i.e. grading) of the angiogenic response and the % N score a measure of the "all or none" response for each sample.

Linear Categorization (Discriminant) Analysis. An unknown compound is assigned by a linear categorizer to a certain class (e.g. angiogenic, or non-angiogenic) when the CAM assay data evaluation leads to a descriptor value (DU) less than a threshold value (T). The DU and T parameters are estimated as follows: The ASI (A) and % N (N) values for each compound are obtained as described above. Next the mean $\overline{A}_I$ and $\overline{N}_I$ values of all samples of class I (e.g. angiogenic) and $\overline{A}_{II}$, $\overline{N}_{II}$ values of all samples of class II (e.g. non-angiogenic) are determined. The $\overline{A}_I$, $\overline{N}_I$ and $\overline{A}_{II}$, $\overline{N}_{II}$ pair values determine the centroids of the distribution of each class of compounds. Subsequently the coordinates $X_1$ and $X_2$ of a symmetrically placed boundary line between the centroids follow as:

$$X_1 = (\overline{A}_{II} + \overline{A}_I)/2$$

$$X_2 = (\overline{N}_{II} + \overline{N}_I)/2$$

The weight coefficients $W_1$ and $W_2$ are estimated by:

$$W_1 = \overline{A}_{II} - \overline{A}_I$$

$$W_2 = \overline{N}_{II} - \overline{N}_I$$

Consequently, the threshold value T is given by:

$$T = X_1 \frac{W_1}{(W_1^2 + W_2^2)^{\frac{1}{2}}} + X_2 \frac{W_2}{(W_1^2 + W_1^2)^{\frac{1}{2}}}$$

The discriminator value DU for a certain compound is computed from:

$$DU = A \frac{W_1}{(W_1^2 + W_2^2)^{\frac{1}{2}}} + N \frac{W_2}{(W_1^2 + W_1^2)^{\frac{1}{2}}}$$

Criteria for Angiogenicity

In order to establish conventional boundaries to evaluate the results of the CAM assay and, thus, being able to classify an amphililic molecule into an "angiogenic" or "non-angiogenic" category, the following experiments were performed. Prostaglandins, a class of lipidic compounds known to be angiogenic were used as positive controls. See i.e., BenEzra, D.; *Am. J. Opthalm.* 86:455 (1978); (neovascularization ability of prostaglandins); Ziche, et al., *J. Natl. Cancer Inst.* 69:475 (1982); (role of prostaglandins in angiogenesis); and Tong, et al., *Fed. Proc.* 44:904 (1985); (effect of prostaglandins on angiogenesis on CAM).

Bovine serum albumin (BSA) dissolved in phosphate buffered saline (PBS) was employed as a negative control. Various prostaglandins (PGE$_1$, PGE$_2$, PGF$_{2a}$, and PGI$_2$ at different concentrations (2.5 to 20 micrograms) were used in order to cover a wide range of angiogenic responses and, thus, obtain a representative sample of ASI and % N values. A total of 167 chick embryos were scored and the results were tabulated as shown in Table IV. Similarly, 47 chick embryos were scored using the BSA/PBS negative controls (see Table IV). A computerized two-dimensional linear categorization technique was then used to obtain a Threshold Boundary T which separates the group of the positive angiogenic samples from the group of negative ones as discussed in Catsimpoolas, et al, *Methods of Cell Separation*, Plenum Press, New York 2:1-63 (1979). Simultaneously a Discriminator Unit (DU) was estimated for each sample. These values are also shown in Table IV.

It was found that the prostaglandin (positive control) group had a centroid with YX coordinates located at A=53.3 and % N=9.4 whereas the centroid of the negative control group was at A=18.4 and % N=83.3. The two groups were distinctly separate with a boundary located at A=35.9 and % N=46.4. As illustrated in FIG. 1 The Threshold Value T was 26.6. That is to say that any sample with a DU value less than 26.6 falls into the positive control group and above 26.6 into the negative control group.

The above convention was then used to classify the amphililic compounds as angiogenically positive or negative, and their relative angiogenic potency. To do this, samples were subjected to the CAM assay and the results were scored. The A and % N scoring values were then estimated and these were entered into the Linear Categorization Computer program to derive the DU value of the sample. The DU value was then compared to the T value by the program and the sample was classified as angiogenically positive or negative. The smaller the DU value, the more angiogenically potent was the sample.

Vascular Perfusion Studies Using Amphiphilic Compounds

Materials and Methods

The following amphiphilic compounds were dissolved in phosphate buffered saline (PBS): digitonin, n-octylglucoside, dodecyl-beta-D-maltoside, sulfobetaine and polyoxyethylene glycol sorbitol. Solutions of the commercially obtained compounds ranged in concentration from 0.25 to 5 mg per ml.

Twenty four cats were chosen for surgical excision to create a need for localized tissue revascularization by a modified method described in Goldsmith, et al., *Surgery* 162:579-583 (Jun. 1986). Also see co-pending U.S. application, Ser. No. 805,206 filed on Dec. 4, 1985 and herein incorporated by reference.

The cats were of both sexes and were anesthetized with an intraperitoneal injection of sodium pentobarbitol (33 milligrams per kilogram). After the cats were anesthetized, a longitudinal skin incision was made in a single hind limb extending from the inguinal crease to the lower portion of the thigh over the femoral vessels. The right or the left hind limbs were alternately operated upon in successive cats during this experiment.

A segment of femoral artery was removed from the inguinal crease to the bifurcation of the femoral artery at the lower end of Hunter's Canal. The divided ends of the femoral artery were ligated with 3-0 silk suture material. The wound was then irrigated with saline solution followed by loose closure of muscle overlying the divided femoral artery using a running 3-0 chromic catgut suture. The skin was approximated with interrupted 3-0 silk sutures. The femoral artery in the limb not operated upon served as the basis for a comparison of nuclear imaging of vascular perfusion.

Injection of the test compounds

Solutions of the compounds in PBS were injected intramuscularly using a No. 19 gauge needle. In all cats, the intramuscular injections were made in and around the area of the femoral artery excision. Approximately 3 milliliters of the test solutions were initially injected on day one followed by injections of 1 milliliter per day for six days for a total of seven days.

Nuclear Imaging Procedures To Demonstrate Vascular Perfusion Differences

Regional vascular perfusion of the hind limbs in this study was demonstrated by tagging erythrocytes of the cats with Technetium (Tc-99 m) with subsequent imaging on a gamma camera coupled to a computer as described in Callahan, et al., *J. Nucl. Med.* 23:315–318 (1982). Nuclear imaging of the hind limbs of the cats was done on day zero (immediately prior to the removal of the femoral artery segment) and on the seventh postoperative day.

The cats were anesthetized by an intraperitoneal injection of sodium pentobarbitol (33 milligrams per kilogram). In preparation for nuclear imaging, a small skin incision was made in a front limb in order to expose a vein suitable for intravenous injection of 500 milligrams of stannous ion administered as PYROLITE ® (stannous pyrophosphate). Twenty minutes later, 10 millicuries of Tc-99 m was injected intravenously. Immediately after the Tc-99 m injection, the cats were imaged anteriorly and posteriorly using an ADAC ARC 3000 gamma camera interfaced with an ADAC 3300 computer system (ADAC Corp.). Each scanning image of the legs (500,000 accumulated counts per image) was stored on a floppy disc for later data retrieval and analysis. Upon retrieval, each image was analyzed using "region of interest" techniques by means of a computer program which determined count data along orthogonal axes. The X-axis traversed both hind limbs and the counts (Y-axis) were displayed in the form of a radiodensity profile along a narrow (3 pixel) horizontal channel. The area of each peak representing the total counts for a particular section of the right and left hind limbs was integrated and the sectional ratio of comparable areas of the surgically operated versus the limb not operated upon was computed for each of the sections. Ten such radio-density profiles were obtained of equidistant sections from each hind limb and the mean ratio (plus or minus standard deviation) for each scan was compiled from the sectional values. Resulting mean values derived from each radiodensity profile formed the basis for evaluating the efficiency of injected omental lipid factor as compared with that of control values; radiodensity being a direct reflection of vascular perfusion present in lower limbs.

Results

Increased blood perfusion observed on the seventh postoperative day are shown in Table III as the radiodensity ratio (R).

It should be noted that all of the amphiphilic compound solutions studied had an effect on the blood perfusion ratio above the baseline of R=1.00. The most pronounced effect on vascular perfusion was observed with the digitonin solution indicating digitonin stimulates a large amount of blood perfusion activity. Further, at the maximum dosage of digitonin compound (i.e. 50 mg per ml) the mean R value was $1.92 \pm 0.47$ as shown in Table III.

A dose-response scattergram is shown in FIG. 2.

It is noted that there were no adverse effects observed with any of the dosages of the compound solutions injected intramuscularly into the twenty-four cats for a period of seven days. These results indicate that at dosage ranges from 2.5 to 50 mg/ml of the five compound solutions studied, no toxicity in mammals occurs.

Conclusion

Of all the amphiphilic compounds tested for angiogenic activity, the most potent angiogenic agent (using the CAM assay and the vascular perfusion studies) was found to be the non-ionic amphiphilic compound digitonin which contains carbohydrate moieties and a hydrophobic residue involving a steriod nucleus.

Compounds With Angiogenic Activity

The following is a list of amphiphilic compounds found to be angiogenic by the inventive method:

A. NON-IONIC AMPHIPHILIC COMPOUNDS:

Digitonin
N-octylglucoside
Polyoxyethylene p't'octyl phenol (Triton-X and Nonidet P-40)
Polyoxyethylene alcohol (Brij 35 and Lubrol Px)
N-dodecyl glucoside
Dodecyl-beta-D-maltoside

B. ANIONIC AMPHIPHILIC COMPOUNDS:

Deoxycholic acid
Sodium dodecylsulfate

C. CATIONIC AMPHIPHILIC COMPOUNDS:

Tetradecyltrimethylammonium bromide

D. ZWITTERIONIC AMPHIPHILIC COMPOUNDS:

Sulfobetaine (Zwittergent)
3-[(3-cholamido propyl) dimethylammonio]-1-propane sulphonate (CHAPS)
Lysophophatidylcholine Compounds Not Exhibiting Angiogenic Activity Amphiphilic compounds found not to possess angiogenic activity at the single dose level tested as indicated (see Table XVI) include:
Cholic acid (50 micrograms)
Taurocholic acid (50 micrograms)
Lubrol PX (polyoxyethylene alchohol) (50 micrograms)
Tween 20, 40, 60, 80 (polyoxyethylene glycol sorbitol) (100 micrograms)

The results of the CAM assays for all of the amphiphilic compounds tested are listed in Tables V-XVI. The angiogenic activity of the non-ionic amphiphilic compounds tested are shown in Tables V-XI; the angiogenic anionic compounds in Tables XII-XIII; and the angiogenic Zwitterionic compounds in Tables XIV-XV. The results of tests at a fixed concentration for a group of amphiphilic compounds are tabulated in Table XVI.

Dose-response value curves for each tested amphiphilic compound were determined from the test results and are illustrated in FIGS. 3-13. The corresponding tabulated results and graphs are as follows:

| Table | FIG. |
|---|---|
| V | 3 |
| VI | 4 |
| VII | 5 |
| VIII | 6 |
| IX | 7 |
| X | 8 |
| XI | 9 |
| XII | 10 |
| XIII | 11 |
| XIV | 12 |
| XV | 13 |

TABLE I
DETERGENTS TESTED

| Detergent type | Structural formula | Formal (and trivial) name |
|---|---|---|
| | DETERGENTS WITH RIGID HYDROPHOBIC REGIONS | |
| Strongly ionic | 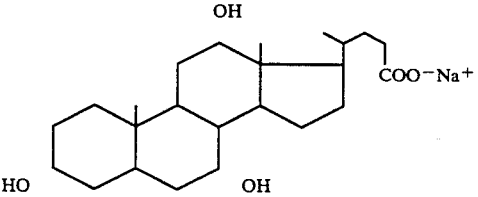 | Sodium cholate (I)* |
| 'Weakly' ionic | 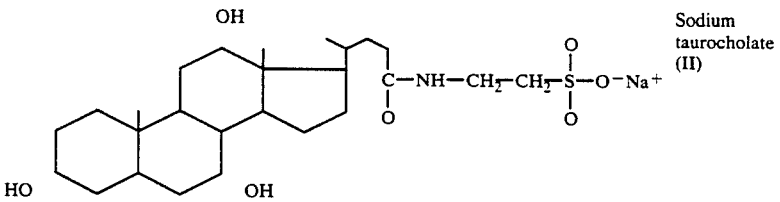 | Sodium taurocholate (II) |
| Zwitterionic | 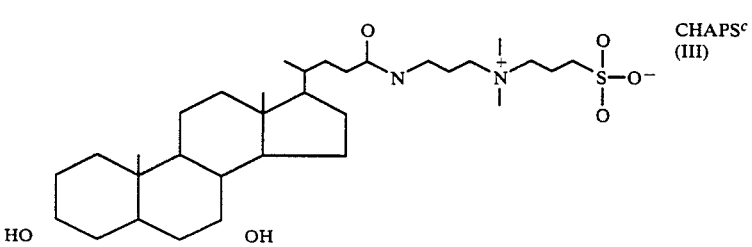 | CHAPS$^c$ (III) |
| Non-ionic | 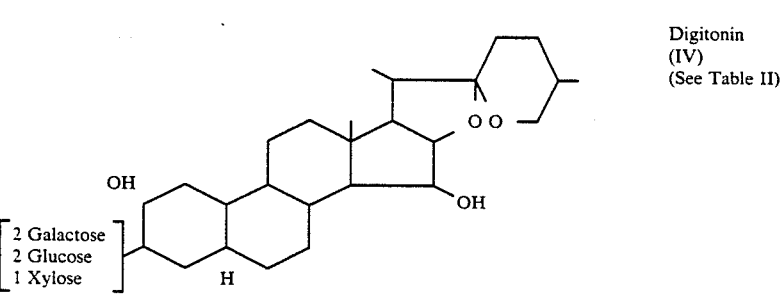 | Digitonin (IV) (See Table II) |
| | DETERGENTS WITH FLEXIBLE HYDROPHOBIC REGIONS | |
| Strongly ionic | 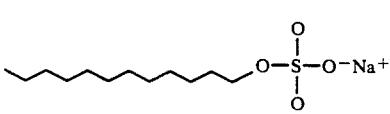 | Sodium dodecylsulphate (V) |
| Zwitterionic | 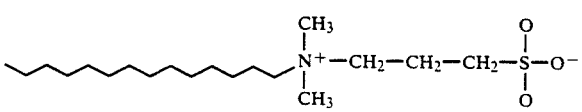 | Sulfobetaine (Zwittergent)$^a$ (VI) Palmitoyllysolecithin |

TABLE I-continued

| Non-ionic | [structure: alkyl chain–O–[CH₂—CH₂—O]ₙH] | Polyoxyethylene alcohol (VII) (Brij series, Lubrol W. AL. P series)* |
|---|---|---|
| | [structure: alkyl–phenyl–O–[CH₂—CH₂—O]ₙH] | Polyoxyethylene nonylphenol (VIII) (Triton N series Igepal CO series Surionic N series Emulgen series) |
| Non-ionic with branched hydrophobic region | [structure: branched alkyl–phenyl–O–[CH₂—CH₂—O]ₙH] | Polyoxyethylene p't'octyl phenol (IX) (Triton X series Igepal CA series Nonide: P40) |

[a] Available from Calbiochem-Behring, Serva.
[b] Available from Onyx Chemical Co., 190 Warren Street, Jersey City NJ 07032 U.S.A.
[c] 3-[(3-cholamidopropyl)dimethylammonio]-1-propanesulphonate, available from Calbiochem-Behring, Serva.
*Roman numeral designation for identification purposes, not part of scientific name
**LUBROX PX, n = 9–10
alkyl-chain, n = 6, 8, 10, 12, 14, 16

DETERGENTS TESTED AND THEIR CHEMICAL STRUCTURE
DETERGENTS WITH FLEXIBLE HYDROPHOBIC REGIONS

| Detergent | Structural formula | Scientific name |
|---|---|---|
| Non-ionic | [structure: octyl–O–glucose ring with CH₂OH, HO, OH, OH] | N-OCTYL GLUCOSIDE (X) |
| | [structure: dodecyl chain–O–Glu] | (XI) |

N-DODECYL GLUCOSIDE

| | [structure: dodecyl chain–β-D-Mal] | (XII) |

N-DODECYL-BETA-D-MALTOSE

DETERGENTS TESTED AND THEIR CHEMICAL STRUCTURE
DETERGENTS WITH FLEXIBLE HYDROPHOBIC REGIONS

| Detergent | Structural formula* | Scientific name |
|---|---|---|
| TWEEN (XIII) | [structure: fatty acyl–C(=O)–O–[CH₂—CH₂—O]ₓ–CH₂–CH–CH–O–[CH₂—CH₂—O]_wH, with O–(CH₂—CH₂—O)_yH branch and CH₂—CH₂—O–[CH₂—CH₂—O]_zH branch] | |

(Aliphatic Chain)
Av. number of ethylene oxide units per ml n = x + y + z + w

| | Aliphatic Chain | |
|---|---|---|
| Tween 20 | monolaureate | (XIV) |
| Tween 40 | monopalmitate | (XV) |
| Tween 60 | monostearate | (XVI) |
| Tween 80 | monooleate | (XVII) |

[Polyoxyethylene glycol (PEG) sorbitol (e.g. monooleate)]

| Anionic | [structure: deoxycholate steroid with HO, HO, carboxylate O⁻] | DEOXYCHOLIC ACID (XVIII) |
| Cationic | [structure: alkyl chain–N⁺(CH₃)₃ Br⁻] | TETRADECYL TRIMETHYL AMMONIUM BROMIDE (XIX) |

TABLE I-continued

Zwitterionic — L-α-LYSOPHOSPHATIDYL CHLOINE (XX)

TABLE II
COMPOSITION OF COMMERCIAL DIGITONIN COMPOSITION or SAPONIN MIXTURE FROM *D. purpurea*

| Name | Genin | Moles sugar per mol genin | Percentage in saponin mixture |
|---|---|---|---|
| Digitonin | Digitogenin | 2 D-Glucose<br>2 D-Galactose<br>1 Xylose | 40 |
| Desglucodigitonin | Digitogenin | 1 Glucose<br>2 Galactose<br>1 Xylose | 25 |
| Digalonin | Digalogenin | 2 Glucose<br>2 Galactose<br>1 Xylose | 15 |
| Gitonin | Gitogenin | 1 Glucose<br>2 Galactose<br>1 Xylose | 15 |
| Tigonin | Tigogenin | 2 Glucose<br>2 Galactose<br>1 Xylose | 3 |
| Other | | | 2 |

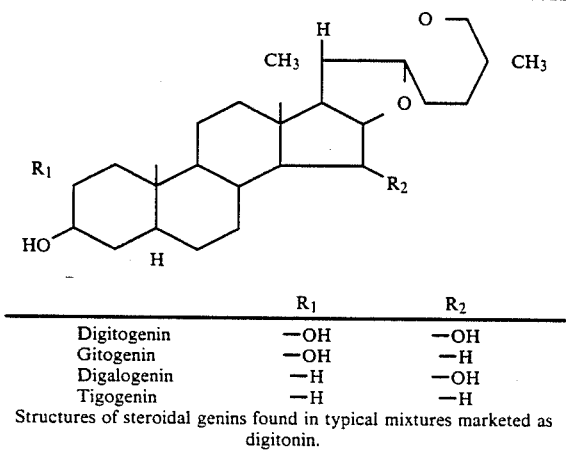

| | $R_1$ | $R_2$ |
|---|---|---|
| Digitogenin | —OH | —OH |
| Gitogenin | —OH | —H |
| Digalogenin | —H | —OH |
| Tigogenin | —H | —H |

Structures of steroidal genins found in typical mixtures marketed as digitonin.

TABLE III
RADIODENSITY RATIO (R) VALUES OBTAINED AFTER I.M. INJECTION OF AMPHIPHILIC COMPOUNDS IN PBS. NUCLEAR SCANS WERE PERFORMED AT DAY 7 POST-OPERATIVE. THE EXPERIMENT INVOLVED TWENTY-FOUR DIFFERENT CATS.

| Compound | Total i.m. dose (mg) | R |
|---|---|---|
| Digitonin | | |
| a. | 2.5 | 1.23 |
| b. | 5.0 | 1.38 |
| c. | 5.0 | 1.41 |
| d. | 7.5 | 1.42 |
| e. | 10.0 | 1.29 |
| f. | 10.0 | 1.84 |
| g. | 15.0 | 1.36 |
| h. | 20.0 | 1.41 |
| i. | 50.0 | 1.32 |
| j. | 50.0 | 1.79 |
| k. | 50.0 | 1.80 |
| l. | 50.0 | 2.94 |
| m. | 50.0 | 1.67 |
| n. | 50.0 | 2.18 |
| o. | 50.0 | 1.55 |

$R = 1.92 \pm 0.47$ for 8 doses of 50 mg ea.

TABLE III-continued
RADIODENSITY RATIO (R) VALUES OBTAINED AFTER I.M. INJECTION OF AMPHIPHILIC COMPOUNDS IN PBS. NUCLEAR SCANS WERE PERFORMED AT DAY 7 POST-OPERATIVE. THE EXPERIMENT INVOLVED TWENTY-FOUR DIFFERENT CATS.

| Compound | Total i.m. dose (mg) | R |
|---|---|---|
| p. | 50.0 | 2.15 |
| Sulfobetaine | | |
| q. | 10.0 | 1.16 |
| r. | 10.0 | 1.35 |
| Polyoxyethylene glycol sorbitol | | |
| s. | 10.0 | 1.20 |
| t. | 10.0 | 1.34 |
| N-Octylglucoside | | |
| u. | 10.0 | 1.22 |
| v. | 30.0 | 1.16 |
| Dodecyl-beta-D-maltoside | | |
| w. | 10.0 | 0.93 |
| x. | 30.0 | 1.22 |

TABLE IV
CRITERIA FOR ANGIOGENCITY

| | | Angiogenic Score | | | | Angio-genicity[a] |
|---|---|---|---|---|---|---|
| Sample | (ug/disc) | Number of CAM tests | ASI | % N | DU | (Yes/No) |
| A. Positive Controls (Prostaglandins) | | | | | | |
| $PGE_1$ | 2.5 | 10 | 42 | 30 | 9.2 | Y |
| $PGE_1$ | 5.0 | 23 | 49 | 9 | −12.8 | Y |
| $PGE_1$ | 7.5 | 8 | 51 | 0 | −21.8 | Y |
| $PGE_1$ | 10.0 | 28 | 61 | 7 | −19.7 | Y |
| $PGE_1$ | 15.0 | 6 | 75 | 0 | −32.0 | Y |
| $PGE_1$ | 20.0 | 4 | 73 | 0 | −31.2 | Y |
| $PGE_2$ | 2.5 | 7 | 44 | 14 | −6.1 | Y |
| $PGE_2$ | 5.0 | 24 | 49 | 4 | −17.3 | Y |
| $PGE_2$ | 10.0 | 10 | 63 | 0 | −26.9 | Y |
| $PGF_{2a}$ | 2.5 | 4 | 50 | 0 | −21.3 | Y |
| $PGF_{2a}$ | 5.0 | 23 | 49 | 9 | −12.8 | Y |
| $PGI_2$ | 5.0 | 20 | 34 | 40 | 21.7 | Y |
| B. Negative Control (BSA/PBS) | | | | | | |
| No. 1 | — | 5 | 15 | 80 | 65.9 | N |
| No. 2 | — | 5 | 21 | 80 | 63.4 | N |
| No. 3 | — | 5 | 16 | 80 | 65.5 | N |
| No. 4 | — | 6 | 24 | 67 | 50.3 | N |
| No. 5 | — | 5 | 16 | 80 | 65.5 | N |
| No. 6 | — | 5 | 18 | 83 | 67.3 | N |
| No. 7 | — | 5 | 15 | 100 | 84.0 | N |
| No. 8 | — | 6 | 20 | 100 | 81.9 | N |
| No. 9 | — | 5 | 21 | 80 | 63.4 | N |

[a]Threshold Value of T = 26.6; if DU is greater than 26.6 the compound is classified as non-angiogenic and if DU is less than 26.6 the compound is classified as angiogenic.

TABLE V
NON-IONIC ANGIOGENIC AMPHIPHILIC COMPOUNDS ANGIOGENIC PROPERTIES OF DIGITONIN - (CAM ASSAY)

| Sample | Amount microgram/disc | Number of CAM assays | Angiogenic Score | | | Angio-genicity (Yes/No) |
|---|---|---|---|---|---|---|
| | | | ASI | % N | DU | |
| a. | 0.600 | 23 | 30.2 | 56 | 35 | N |
| b. | 1.250 | 20 | 41.7 | 15 | −7 | Y |

TABLE V-continued

NON-IONIC ANGIOGENIC AMPHIPHILIC COMPOUNDS ANGIOGENIC PROPERTIES OF DIGITONIN - (CAM ASSAY)

| Sample | Amount microgram/ disc | Number of CAM assays | Angiogenic Score ASI | % N | DU | Angiogenicity (Yes/No) |
|---|---|---|---|---|---|---|
| c. | 3.125 | 19 | 39.7 | 32 | 8 | Y |
| d. | 6.250 | 13 | 41.6 | 23 | 0 | Y |
| e. | 9.375 | 18 | 43.4 | 6 | −16 | Y |
| f. | 12.500 | 21 | 47.1 | 14 | −10 | Y |
| g. | 25.000 | 8 | 54.2 | 0 | −26 | Y |
| h. | 50.000 | 11 | 52.2 | 0 | −25 | Y |
| i. | 100.000 | 15 | 61.8 | 0 | −30 | Y |
| j. | 150.000 | 8 | 65.0 | 0 | −32 | Y |
| k. | 200.000 | 11 | 69.8 | 0 | −34 | Y |

TABLE VI

ANGIOGENIC PROPERTIES OF N-OCTYLGLUCOSIDE (CAM ASSAY)

| Sample | Amount microgram/ disc | Number of CAM assays | Angiogenic Score ASI | % N | DU | Angiogenicity (Yes/No) |
|---|---|---|---|---|---|---|
| a. | 12.5 | 8 | 37.5 | 25 | 4 | Y |
| b. | 25 | 5 | 38.7 | 20 | −1 | Y |
| c. | 50 | 4 | 53.4 | 0 | −26 | Y |
| d. | 100 | 6 | 49.0 | 17 | −9 | Y |
| e. | 150 | 5 | 49.4 | 0 | −24 | Y |
| f. | 200 | 8 | 53.4 | 0 | −26 | Y |

TABLE VII

ANGIOGENIC PROPERTIES OF N-DODECYL GLUCOSIDE (CAM ASSAY)

| Sample | Amount microgram/ disc | Number of CAM assays | Angiogenic Score ASI | % N | DU | Angiogenicity (Yes/No) |
|---|---|---|---|---|---|---|
| a. | 12.5 | 11 | 24.9 | 64 | 43 | N |
| b. | 25.0 | 10 | 32.7 | 40 | 19 | Y |
| c. | 50.0 | 8 | 40.1 | 12 | −9 | Y |
| d. | 100.0 | 12 | 45.0 | 17 | −7 | Y |
| e. | 150.0 | 14 | 37.7 | 29 | 7 | Y |
| f. | 200.0 | 12 | 31.7 | 50 | 28 | N |

TABLE VIII

ANGIOGENIC PROPERTIES OF DODECYL-BETA-D-MALTOSIDE (CAM ASSAY)

| Sample | Amount microgram/ disc | Number of CAM assays | Angiogenic Score ASI | % N | DU | Angiogenicity (Yes/No) |
|---|---|---|---|---|---|---|
| a. | 12.5 | 12 | 22.3 | 83 | 62 | N |
| b. | 25 | 14 | 44.8 | 7 | −15 | Y |
| c. | 50 | 14 | 49.1 | 0 | −24 | Y |
| d. | 100 | 10 | 37.4 | 20 | −1 | Y |
| e. | 150 | 14 | 57.7 | 0 | −28 | Y |
| f. | 200 | 8 | 58.4 | 0 | −28 | Y |

TABLE IX

ANGIOGENIC PROPERTIES OF POLYOXYETHYLENE p't' OCTYLPHENOL (CAM ASSAY) (TRITON-X)

| Sample | Amount microgram/ disc | Number of CAM assays | Angiogenic Score ASI | % N | DU | Angiogenicity (Yes/No) |
|---|---|---|---|---|---|---|
| a. | 12.5 | 15 | 27.2 | 60 | 39 | N |
| b. | 25.0 | 15 | 32.5 | 47 | 25 | Y |
| c. | 50 | 12 | 30.6 | 58 | 36 | N |
| d. | 100 | 16 | 52.6 | 0 | −26 | Y |
| e. | 150 | 14 | 52.0 | 7 | −19 | Y |
| f. | 200 | 13 | 59.1 | 0 | −29 | Y |

TABLE X

ANGIOGENIC PROPERTIES OF POLYOXYETHYLENE p't' OCTYLPHENOL (CAM ASSAY) (NONIDET-P40)

| Sample | Amount microgram/ disc | Number of CAM assays | Angiogenic Score ASI | % N | DU | Angiogenicity (Yes/No) |
|---|---|---|---|---|---|---|
| a. | 12.5 | 7 | 29.6 | 43 | 23 | Y |
| b. | 25 | 10 | 34.0 | 50 | 27 | N |
| c. | 50 | 9 | 20.0 | 78 | 58 | N |
| d. | 100 | 8 | 44.3 | 12 | −11 | Y |
| e. | 150 | 10 | 61.4 | 0 | −30 | Y |
| f. | 200 | 12 | 66.7 | 0 | −32 | Y |

TABLE XI

ANGIOGENIC PROPERTIES OF POLYOXYETHYLENE ALCOHOL (Brij 35) (CAM ASSAY)

| Sample | Amount microgram/ disc | Number of CAM assays | Angiogenic Score ASI | % N | DU | Angiogenicity (Yes/No) |
|---|---|---|---|---|---|---|
| a. | 12.5 | 16 | 28.3 | 50 | 30 | N |
| b. | 25 | 16 | 38.4 | 37 | 14 | Y |
| c. | 50 | 15 | 45.0 | 20 | −4 | Y |
| d. | 100 | 14 | 45.8 | 14 | −10 | Y |
| e. | 150 | 13 | 55.9 | 0 | −27 | Y |
| f. | 200 | 13 | 61.1 | 0 | −30 | Y |

TABLE XII

ANIONIC ANGIOGENIC AMPHIPHILIC COMPOUNDS ANGIOGENIC PROPERTIES OF SODIUM DODECYLSULFATE (CAM ASSAY)

| Sample | Amount microgram/ disc | Number of CAM assays | Angiogenic Score ASI | % N | DU | Angiogenicity (Yes/No) |
|---|---|---|---|---|---|---|
| a. | 12.5 | 12 | 33.9 | 42 | 20 | Y |
| b. | 25 | 7 | 41.0 | 29 | 5 | Y |
| c. | 50 | 13 | 51.3 | 0 | −25 | Y |
| d. | 100 | 8 | 55.9 | 0 | −27 | Y |
| e. | 150 | 10 | 63.4 | 0 | −31 | Y |
| f. | 200 | 10 | 58.7 | 10 | −20 | Y |

TABLE XIII

ANGIOGENIC PROPERTIES OF DEOXYCHOLIC ACID (CAM ASSAY)

| Sample | Amount microgram/ disc | Number of CAM assays | Angiogenic Score ASI | % N | DU | Angiogenicity (Yes/No) |
|---|---|---|---|---|---|---|
| a. | 12.5 | 11 | 35.2 | 45 | 23 | Y |
| b. | 25 | 12 | 35.6 | 42 | 19 | Y |
| c. | 50 | 14 | 38.7 | 36 | 12 | Y |
| d. | 100 | 13 | 51.9 | 15 | −12 | Y |
| e. | 150 | 11 | 61.9 | 0 | −31 | Y |
| f. | 200 | 11 | 58.8 | 0 | −29 | Y |

TABLE XIV

ZWITTERIONIC ANGIOGENIC AMPHIPHILIC COMPOUNDS
ANGIOGENIC PROPERTIES OF
SULFOBETAINE (ZWITTERGENT C-16) (CAM ASSAY)

| Sample | Amount microgram/disc | Number of CAM assays | Angiogenic Score ASI | % N | DU | Angiogenicity (Yes/No) |
|---|---|---|---|---|---|---|
| a. | 25 | 8 | 35.9 | 38 | 15 | Y |
| b. | 50 | 14 | 52.5 | 0 | −25 | Y |
| c. | 75 | 8 | 57.5 | 0 | −28 | Y |
| d. | 100 | 12 | 61.7 | 0 | −30 | Y |
| e. | 125 | 12 | 57.3 | 0 | −28 | Y |
| f. | 150 | 8 | 59.2 | 0 | −29 | Y |
| g. | 175 | 8 | 70.9 | 0 | −34 | Y |
| h. | 200 | 10 | 58.1 | 0 | −28 | Y |

TABLE XV

ANGIOGENIC PROPERTIES OF
3-[3-CHOLAMIDO PROPYL) DIMETHYLAMMONIO]
-1-PROPANESULPHONATE (CHAPS) (CAM ASSAY)

| Sample | Amount microgram/disc | Number of CAM assays | Angiogenic Score ASI | % N | DU | Angiogenicity (Yes/No) |
|---|---|---|---|---|---|---|
| a. | 12.5 | 6 | 42.3 | 33 | 9 | Y |
| b. | 25 | 16 | 49.3 | 0 | −24 | Y |
| c. | 50 | 12 | 46.2 | 8 | −15 | Y |
| d. | 100 | 11 | 46.1 | 9 | −14 | Y |
| e. | 150 | 15 | 52.1 | 0 | −25 | Y |
| f. | 200 | 14 | 65.8 | 0 | −32 | Y |

TABLE XVI

ANGIOGENIC PROPERTIES OF
AMPHIPHILIC COMPOUNDS
TESTED AT A FIXED CONCENTRATION

| Sample | Amount microgram/disc | Number of CAM assays | Angiogenic Score ASI | % N | DU | Angiogenicity (Yes/No) |
|---|---|---|---|---|---|---|
| A. Non-ionic | | | | | | |
| Lubrol PX | 50 | 13 | 24.6 | 77 | 55 | N |
| Tween 20 | 100 | 14 | 25.8 | 71 | 50 | N |
| Tween 40 | 100 | 8 | 20.0 | 75 | 56 | N |
| Tween 60 | 100 | 12 | 23.9 | 58 | 39 | N |
| Tween 80 | 100 | 10 | 25.4 | 60 | 40 | N |
| B. Anionic | | | | | | |
| Cholic acid | 50 | 10 | 23.8 | 90 | 67 | N |
| Taurocholic Acid | 50 | 9 | 19.1 | 78 | 59 | N |
| C. Cationic | | | | | | |
| Tetradecyl-trimethyl-ammonium bromide | 37 | 12 | 44.3 | 17 | −7 | Y |
| | 67 | 8 | 51.0 | 0 | −25 | Y |
| D. Zwitterionic | | | | | | |
| L-lysophosphatidyl-choline | 67 | 7 | 39.1 | 0 | −19 | Y |
| Zwittergent C-8 | 100 | 11 | 27.9 | 45 | 26 | Y |
| Zwittergent C-10 | 100 | 10 | 30.7 | 50 | 29 | N |
| Zwittergent C-12 | 100 | 11 | 41.9 | 27 | 3 | Y |
| Zwittergent C-14 | 100 | 15 | 58.7 | 0 | −28 | Y |

What is claimed is:

1. Method for enhancing angiogenesis or vascular perfusion in a mammal comprising:
   administering an amount of at least one angiogenically active non-ionic amphiphilic compound selected from the group consisting of digitonin, n-octylglucoside, polyoxyethylene p't'octyl phenol, polyoxyethylene alcohol, n-dodecyl glucoside and dodecyl-beta-D-maltoside to a mammal in need of enhanced angiogenesis or vascular perfusion in an amount sufficient to enhance angiogenesis or vascular perfusion.

2. Method according to claim 1, wherein said non-ionic amphiphilic compound contains a glucoside group.

3. Method for enhancing angiogenesis in a mammal comprising:
   administering to a mammal in need of enhanced angiogenesis an amount of deoxycholic acid or sodium dodecyl sulfate sufficient to enhance angiogenesis.

4. Method for enhancing angiogenesis in a mammal comprising:
   administering to a mammal in need of enhanced angiogenesis an amount of tetradecyltrimethylammonium bromide sufficient to enhance angiogenesis.

5. Method for enhancing angiogenesis in a mammal comprising:
   administering to a mammal in need of angiogenesis an amount of at least one angiogenically active zwitterionic amphiphilic compound selected from the group consisting of sulfobetaine, 3-[(3-cholamido propyl)dimethylammonio]-1-propanesulphonate and lysophosphatidylcholine sufficient to enhance angiogenesis.

6. Method according to claim 1, wherein said compound is digitonin and is administered in an amount ranging from 1.25 micrograms to 50 mg.

7. Method according to claim 1 for enhancing vascular blood perfusion in a mammal comprising:
   administering to a mammal in need of enhanced blood perfusion an amount of at least one angiogenically active non-ionic, or zwitterionic amphiphilic compound selected from the group consisting of digitonin, sulfobetaine, polyoxyethylene glycol sorbitol, N-octylglucoside and dodecyl-beta-D-maltoside, sufficient to enhance vascular perfusion.

8. Method of claim 7 wherein said compound is digitonin.